(12) United States Patent
Kwon et al.

(10) Patent No.: US 11,229,363 B2
(45) Date of Patent: Jan. 25, 2022

(54) APPARATUS AND METHOD FOR DETECTING BIOLOGICAL INFORMATION

(71) Applicant: SAMSUNG ELECTRONICS CO., LTD., Suwon-si (KR)

(72) Inventors: Yongjoo Kwon, Yongin-si (KR); Jaemin Kang, Seoul (KR); Sunkwon Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/540,738

(22) Filed: Aug. 14, 2019

(65) Prior Publication Data

US 2019/0365231 A1    Dec. 5, 2019

Related U.S. Application Data

(62) Division of application No. 15/013,385, filed on Feb. 2, 2016, now Pat. No. 10,420,470.

(30) Foreign Application Priority Data

Jul. 3, 2015 (KR) .................. 10-2015-0095198

(51) Int. Cl.
*A61B 5/024* (2006.01)
*A61B 5/00* (2006.01)
(Continued)

(52) U.S. Cl.
CPC .............. *A61B 5/0059* (2013.01); *A61B 5/02* (2013.01); *A61B 5/02007* (2013.01);
(Continued)

(58) Field of Classification Search
CPC ..... A61B 5/02; A61B 5/02007; A61B 5/0261; A61B 5/02416; A61B 5/0059;
(Continued)

(56) References Cited

U.S. PATENT DOCUMENTS 7,470,235 B2   12/2008  Moriya et al.
7,544,168 B2   6/2009   Nitzan
(Continued)

FOREIGN PATENT DOCUMENTS

CN   102395311 A   3/2012
CN   103610467 A   3/2014
(Continued)

OTHER PUBLICATIONS

Communication dated Mar. 24, 2020 issued by the European Patent Office in European Application No. 16158647.4.
(Continued)

*Primary Examiner* — George R Evanisko
(74) *Attorney, Agent, or Firm* — Sughrue Mion, PLLC

(57) ABSTRACT

Provided are apparatuses and methods for detecting biological information. An apparatus for detecting biological information may include a biological signal measurement unit having at least two light emission elements having different light emission angles. The at least two light emission elements may include different types of light sources. The at least two light emission elements may include multiple light sources of the same type, and in this case, an optical element configured to adjust a light emission angle of one of the light sources may be provided. The apparatus for detecting biological information may include a biological signal measurement unit including a light emitting unit having variable light emission angle. The apparatus for detecting biological information may further include a data processor configured to extract and analyze biological information of a subject from data measured by the biological signal measurement unit.

12 Claims, 59 Drawing Sheets

(51) Int. Cl.
  *A61B 5/1455* (2006.01)
  *A61B 5/02* (2006.01)

(52) U.S. Cl.
  CPC ...... *A61B 5/02427* (2013.01); *A61B 5/14552* (2013.01); *A61B 5/6826* (2013.01)

(58) Field of Classification Search
  CPC ... A61B 5/0062; A61B 5/0064; A61B 5/0066; A61B 5/0068
  See application file for complete search history.

(56) References Cited

U.S. PATENT DOCUMENTS

| | | | |
|---|---|---|---|
| 10,548,491 B2 * | 2/2020 | Paulussen | A61B 5/14552 |
| 2006/0094941 A1 * | 5/2006 | Cho | A61B 5/1455 600/316 |
| 2008/0180950 A1 | 7/2008 | Kang et al. | |
| 2008/0275317 A1 | 11/2008 | Cho et al. | |
| 2009/0048489 A1 | 2/2009 | Igarashi et al. | |
| 2012/0016210 A1 | 1/2012 | Kim et al. | |
| 2013/0229285 A1 | 9/2013 | Watson et al. | |
| 2014/0200423 A1 | 7/2014 | Eisen et al. | |
| 2016/0058309 A1 * | 3/2016 | Han | A61B 5/0261 600/479 |
| 2016/0206221 A1 | 7/2016 | Kim et al. | |
| 2016/0206251 A1 | 7/2016 | Kwon et al. | |
| 2016/0296174 A1 * | 10/2016 | Isikman | A61B 5/7214 |

FOREIGN PATENT DOCUMENTS

| | | |
|---|---|---|
| CN | 103906468 A | 7/2014 |
| GB | 2519335 A | 4/2015 |
| JP | 2003-52652 A | 2/2003 |
| JP | 2006-102159 A | 4/2006 |
| JP | 2012-50746 A | 3/2012 |
| JP | 2012-191969 A | 10/2012 |
| KR | 10-0438839 B1 | 7/2004 |
| KR | 10-0785279 B1 | 12/2007 |
| KR | 10-0820159 B1 | 4/2008 |
| KR | 10-2008-0086853 A | 9/2008 |
| KR | 10-0944710 B1 | 2/2010 |
| KR | 10-2011-0133576 A | 12/2011 |
| KR | 10-2016-0090125 A | 7/2016 |
| WO | 2015084375 A1 | 6/2015 |

OTHER PUBLICATIONS

Communication dated Apr. 17, 2020 issued by the State Intellectual Property Office of P.R. China in Chinese Application No. 201610236940.X.

Communication dated Dec. 2, 2016 issued by the European Patent Office in counterpart European Patent Application No. 16158647.4.

L.G. Commander et al., "Variable focal length microlenses", Optics Communications, vol. 177, Elsevier Science B.V., Apr. 15, 2000, pp. 157-170.

Communication dated Oct. 28, 2021, issued by the Korean Intellectual Property Office in Korean Patent Application No. 10-2015-0095198.

* cited by examiner

FIG. 35
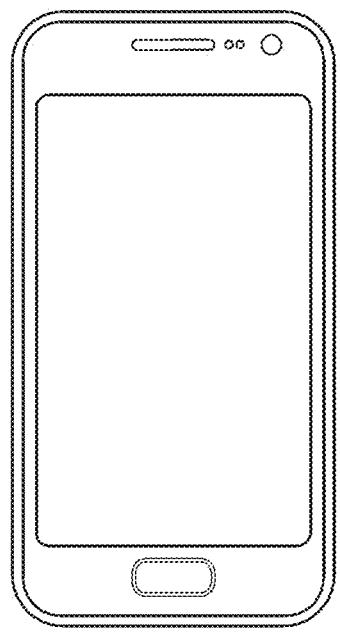
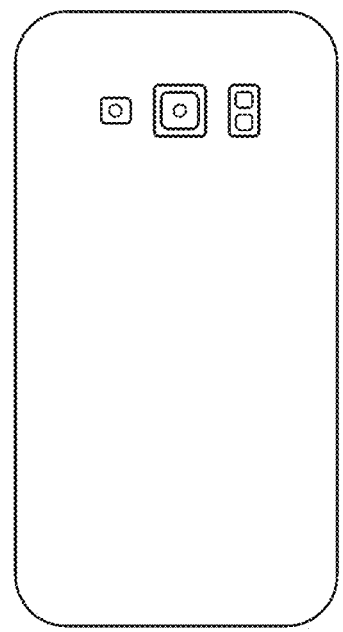
<FRONT SURFACE>    <REAR SURFACE>

APPARATUS AND METHOD FOR DETECTING BIOLOGICAL INFORMATION

CROSS-REFERENCE TO RELATED APPLICATION(S)

This is a Divisional Application of U.S. application Ser. No. 15/013,385, filed on Feb. 2, 2016, which claims the benefit of Korean Patent Application No. 10-2015-0095198, filed on Jul. 3, 2015, in the Korean Intellectual Property Office, the disclosure of which is incorporated herein in its entirety by reference.

BACKGROUND

1. Field

Apparatuses, systems, and methods consistent with exemplary embodiments relate detecting biological information.

2. Description of the Related Art

As medical science has progressed and average life expectancy has increased, an interest in health care has increased. Also, interest in medical equipment/devices has increased to extend not only to various types of medical equipment used in hospitals or health examination facilities, but also to middle- or small-sized types of medical equipment provided for use in public facilities and compact medical equipment and health-care apparatuses that may be kept at home or carried by individuals.

Biological information of a subject may be detected by an invasive method or a non-invasive method. Using a non-invasive method, biological information may be detected in a relatively simple manner without causing pain to a subject. However, when biological information is detected using a non-invasive method, it may be difficult to guarantee the accuracy and precision of the detection results.

SUMMARY

One or more exemplary embodiments may provide apparatuses, systems and methods for detecting biological information, whereby biological information of a subject may be easily detected.

One or more exemplary embodiments may provide apparatuses, systems and methods for detecting biological information, whereby the detection accuracy and reliability may be improved.

Additional exemplary aspects and advantages will be set forth in part in the description which follows and, in part, will be apparent from the description, or may be learned by practice of the presented exemplary embodiments.

According to an aspect of an exemplary embodiment, an apparatus for detecting biological information includes a biological signal measurement unit including a light emission portion and a photodetector, the light emission portion including at least two light emission elements having light emission angles of different sizes, the photodetector being configured to detect light generated by the light emission portion and modulated by a subject, and a data processor configured to extract and analyze biological information of the subject from data measured by the biological signal measurement unit.

The at least two light emission elements may include a first light emission element and a second light emission element, the first light emission element may include a first light source, the second light emission element may include a second light source of a different type with respect to the first light source, and the first light source and the second light source may have different light emission angles.

A light emission angle of one of the first light source and the second light source may range from about 0° to about 90°, and a light emission angle of the other may range from about 80° to about 180°.

One of the first light source and the second light source may be a laser diode (LD), and the other may be a light emitting diode (LED).

The at least two light emission elements may include a first light emission element and a second light emission element, the first light emission element may include a first light source, the second light emission element may include a second light source of a same type with respect to the first light source, and one of the first light emission element and the second light emission element may further include an optical element configured to adjust a light emission angle of light generated by the light source thereof.

The optical element may include at least one of a lens, an optical waveguide, a slit, a concave mirror, and a convex mirror.

One of the first light emission element and the second light emission element may include the optical element and the other of the first light emission element and the second light emission element may not include the optical element.

The first light emission element may include a first optical element corresponding to the optical element, and the second light emission element may include a second optical element different from the first optical element.

The at least two light emission elements may include a first light emission element and a second light emission elements, a light emission angle of one of the first and second light emission elements may range from about 0° to about 90°, and a light emission angle of the other of the first and second light emission elements may range from about 80° to about 180°.

The data processor may be configured to select a signal having a relatively high signal-to-noise ratio (SNR) from among a plurality of detected signals measured by the at least two light emission elements and to extract and analyze biological information of the subject using the selected signal.

The at least two light emission elements may include a first light emission element and a second light emission element, and the photodetector may include at least one light receiving device configured to receive both of an optical signal based on light emitted by the first light emission element and an optical signal based on light emitted by the second light emission element.

The at least two light emission elements may include a first light emission element and a second light emission element, the photodetector may include at least one first light receiving device and at least one second light receiving device, and the first light receiving device may be configured to selectively receive an optical signal generated by light output by the first light emission element, and the second light receiving device is configured to selectively receive an optical signal generated by light output by the second light emission element.

The first light emission element may generate light of a first wavelength range, and the second light emission element may generate light of a second wavelength range different from the first wavelength range, and the first light receiving device may be configured to receive an optical signal corresponding to the first wavelength range, and the second light receiving device is configured to receive an optical signal corresponding to the second wavelength range.

The photodetector may include a plurality of light receiving devices, and the plurality of light receiving devices may be disposed in an array surrounding at least a part of the light emission portion.

The photodetector may include a plurality of device regions around the light emission portion, and each of the device regions may include a plurality of light receiving devices and the plurality of light receiving devices may be configured to receive light of different wavelength ranges.

The light emission portion may include a plurality of first light emission elements having a first light emission angle and a plurality of second light emission elements having a second light emission angle, and the plurality of first light emission elements and the plurality of second light emission elements may be alternately arranged in a two-dimensional array.

The light emission portion and the photodetector corresponding to the light emission portion may constitute one sub-unit, and the biological signal measurement unit may comprise an array of a repeating arrangement of a plurality of the sub-units.

The biological signal measurement unit may be configured to measure an effective measurement surface of the subject via a non-contact method.

The biological signal measurement unit may further include at least one spacer protruding toward one side of the biological signal measurement unit, in which the at least one spacer separates the light emission portion and photodetector from a surface of the subject.

The biological signal measurement unit may be configured to measure a surface pulse wave and/or photoplethysmogram (PPG) of the subject.

Biological information detected by the apparatus for detecting biological information may include at least one of a blood pressure, a heart rate, a blood oxygen saturation, a blood vessel elasticity, a blood flow rate, and arterial stiffness.

The apparatus may further include a light source driver connected to the biological signal measurement unit, and a signal converter connected between the biological signal measurement unit and the data processor.

The apparatus may further include a processor, in which the processor includes the data processor and a controller.

At least a part of the apparatus for detecting biological information may constitute at least a part of a portable device or a wearable device.

According to an aspect of another exemplary embodiment, an apparatus for detecting biological information includes a biological signal measurement unit including a light emission portion and a photodetector, the light emission portion including at least one light emitting unit having a variable light emission angle, the at least one light emitting unit including a light source and a light emission angle control element configured to control a light emission angle of the light source, the photodetector detecting light generated by the light emission portion and modulated by a subject, and a data processor configured to extract and analyze biological information of the subject from data measured by the biological signal measurement unit.

The light emission angle control element may include a variable focusing lens.

The light emission angle control element may include one of an auto focusing module (AFM) comprising a voice coil motor (VCM), a liquid lens using comprising electrowetting unit, and a variable focal length microlens comprising liquid crystal.

A light emission angle of the light emitting unit may be controlled according to a distance between the light source and the subject.

The apparatus may further include a distance measuring sensor configured to measure a distance between the light source and the subject.

The data processor may be configured to select a signal having a relatively high signal-to-noise ratio (SNR) from among a plurality of detected signals measured while changing a light emission angle of the light emitting unit.

The photodetector may include a plurality of light receiving devices, and the plurality of light receiving devices may be disposed in an array surrounding at least a part of the light emission portion.

The light emission portion may include a plurality of the light emitting units, and/or the light emission portion may further include at least one light emission element having a fixed light emission angle.

The biological signal measurement unit may be configured to measure a surface pulse wave and/or photoplethysmogram (PPG) of the subject.

Biological information detected by the apparatus for detecting biological information may include at least one of a blood pressure, a heart rate, a blood oxygen saturation, a blood vessel elasticity, a blood flow rate, and arterial stiffness.

According to an aspect of another exemplary embodiment, a method of detecting biological information includes irradiating a measurement area of a subject with incident light from at least two light emission elements having different light emission angles, generating a plurality of signals from light output by the at least two light emission elements and modulated by the measurement area, and selecting a signal having a relatively high signal-to-noise ratio (SNR) from among a plurality of generated signals, and extracting and analyzing biological information of the subject using the selected signal.

The light may be irradiated onto the measurement area of the subject by driving the at least two light emission elements to emit light at different times, and the plurality of signals may be detected at different times, corresponding to the different times at which the light is emitted from the at least two light emission elements.

The light may irradiated onto the measurement area of the subject by simultaneously driving the at least two light emission elements, and the plurality of signals may be detected using a plurality of light receiving devices different from each other.

The at least two light emission elements may include a first light emission element and a second light emission element, the first light emission element may include a first light source, and the second light emission element may include a second light source of a different type with respect to the first light source, and the first light source and the second light source may have different light emission angles.

At least two light emission elements may include a first light emission element and a second light emission element, the first light emission element may include a first light source, and the second light emission element may include a second light source of same type as the first light source, and one of the first light emission element and the second light emission element may further include a lens configured to condense or disperse light generated by the light source thereof.

According to an aspect of another exemplary embodiment, a method of detecting biological information may include irradiating a measurement area of a subject with light output by at least one light emitting unit having variable light emission angle, the at least one light emitting unit including a light source and a light emission angle control element configured to control a light emission angle of the light source, generating a signal from light incident on and modulated by the measurement area, and extracting and analyzing biological information of the subject using the generated signal.

The method may further include measuring a distance between the light source and the subject, and changing a light emission angle of the light emitting unit according to the measured distance.

A plurality of signals corresponding to a plurality of light emission angles may be generated from light detected while changing a light emission angle of the light emitting unit, and after a signal having a relatively high signal-to-noise ratio (SNR) may be selected from among the generated signals, biological information of the subject is extracted and analyzed using the selected signal.

The light emission angle control element may include a variable focusing lens.

BRIEF DESCRIPTION OF THE DRAWINGS

These and/or other exemplary aspects will become apparent and more readily appreciated from the following description of exemplary embodiments, taken in conjunction with the accompanying drawings in which:

FIG. 35 illustrates an example of a portable device for use with the apparatus for detecting biological information, according to an exemplary embodiment;

DETAILED DESCRIPTION

Figure 1:
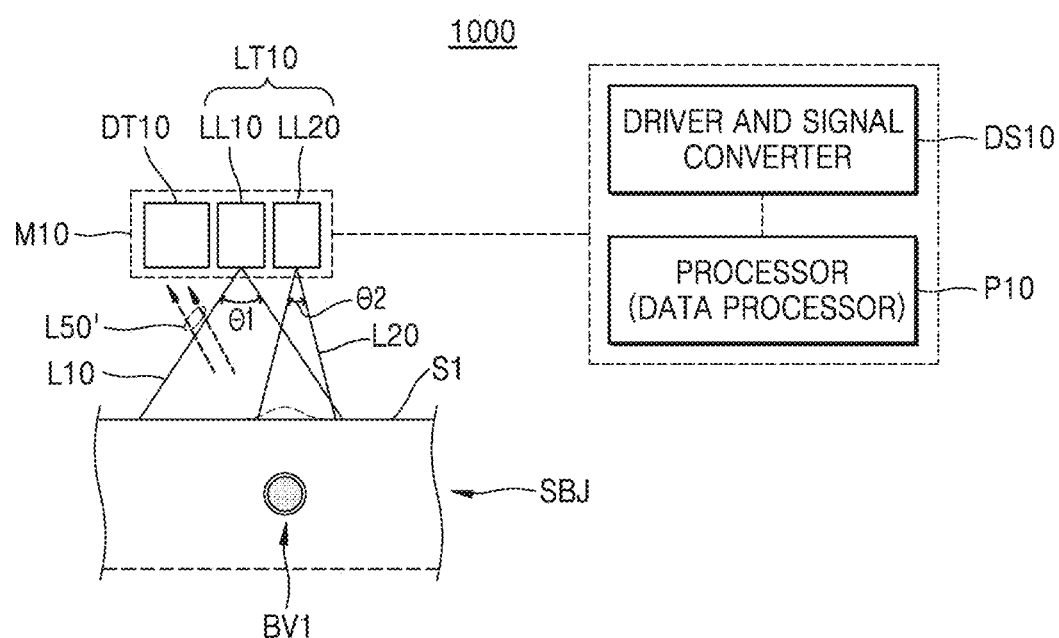
FIG. 1 schematically illustrates a structure of an apparatus for detecting biological information, according to an exemplary embodiment.

Various exemplary embodiments will now be described more fully with reference to the accompanying drawings in which exemplary embodiments are shown.

It should be understood that when an element is referred to herein as being "connected" or "coupled" to another element, it can be directly connected or coupled to the other element, or intervening elements may be present. In contrast, when an element is referred to as being "directly connected" or "directly coupled" to another element, there are no intervening elements present. As used herein the term "and/or" includes any and all combinations of one or more of the associated listed items.

It should be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular exemplary embodiments only and is not intended to be limiting of the exemplary embodiments. As used herein, the singular forms "a," "an" and "the" are intended to include the plural forms as well, unless the context clearly indicates otherwise. It should be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Exemplary embodiments are described herein with reference to cross-sectional illustrations that are schematic illustrations of idealized aspects (and intermediate structures) of exemplary embodiments. As such, variations from the shapes of the illustrations as a result, for example, of manufacturing techniques and/or tolerances, are to be expected. Thus, exemplary embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of exemplary embodiments.

Unless otherwise defined, all terms (including technical and scientific terms) used herein have the same meaning as commonly understood by one of ordinary skill in the art to which exemplary embodiments belong. It should be further understood that terms, such as those defined in commonly-used dictionaries, should be interpreted as having a meaning that is consistent with their meaning in the context of the relevant art and will not be interpreted in an idealized or overly formal sense unless expressly so defined herein.

Reference will now be made in detail to an apparatus and system for detecting biological information and a method of detecting biological information, examples of which are illustrated in the accompanying drawings, wherein like reference numerals refer to like elements throughout. Also, the size of each element (or unit) illustrated in the drawings may be exaggerated for convenience of explanation and clarity. In this regard, the presented exemplary embodiments may have different forms and should not be construed as being limited to the descriptions set forth herein. Accordingly, the exemplary embodiments are merely described below, by referring to the figures, to explain aspects of the present description. In a structure, when a constituent element is disposed "above" or "on" to another constituent element, the constituent element may be only directly on the other constituent element or above the other constituent elements in a non-contact manner.

Hereinafter, an apparatus and system for detecting biological information and a method of detecting biological information will be described more fully with reference to the accompanying drawings. The width and thickness of a layer or region illustrated in the drawings may be rather exaggerated for convenience of explanation. Like reference numerals in the drawings denote like elements, throughout the following description.

FIG. 1 schematically illustrates a structure of a biological information detection apparatus 1000, according to an exemplary embodiment. The term "biological information" may signify information of a living body. The biological information may include biological and medical information that may be obtained from a body of a subject SBJ, for example, a living thing such as a human or an animal, which is a measurement subject of the biological information detection apparatus 1000, or a partial element or component of the body.

Referring to FIG. 1, the biological information detection apparatus 1000 may include a biological signal measurement unit M10 to measure a biological signal of the SBJ. Also, the biological information detection apparatus 1000 may include a non-volatile memory (not shown) storing instructions and a data processor configured to execute the instructions and thereby extract and analyze biological information of the subject SBJ from data measured by the biological signal measurement unit M10. The data processor may be provided within a processor (processor unit) P10. Also, the biological information detection apparatus 1000 may further include a driver and signal converter DS10 connected to the processor P10 of the biological signal measurement unit M10. The driver and signal converter DS10 may include a light source driver and a signal converter.

The biological signal measurement unit M10 may include a light emission portion LT10 to irradiate predetermined light onto a measurement area of the subject SBJ. The light emission portion LT10 may include at least two light emission elements LL10 and LL20 having light emission angles of different sizes. For example, the light emission portion LT10 may include a first light emission element LL10 having a first light emission angle $\theta1$ within which light is emitted and a second light emission element LL20 having a second light emission angle $\theta2$ within which light is emitted. The first light emission angle $\theta1$ and the second light emission angle $\theta2$ may be different from each other. For example, the first light emission angle $\theta1$ may be greater than the second light emission angle $\theta2$ by about 20° or more, or about 40° or more. In a detailed example, the first light emission angle $\theta1$ may be about 60° to 180°, and the second light emission angle $\theta2$ may be about 0° to 100°. Alternatively, the first light emission angle $\theta1$ may be about 80° to 180°, and the second light emission angle $\theta2$ may be about 0° to 90°. Alternatively, the first light emission angle $\theta1$ may be about 100° to 170°, and the second light emission angle $\theta2$ may be about 5° to 50°. The ranges of the first and second light emission angles $\theta1$ and $\theta2$ are exemplary and may vary. The term "light emission angle" describes an angle defining a degree of spreading of light output by a light source in a predetermined direction toward the sides (to the periphery) with respect to the irradiation direction. Accordingly, the "light emission angle" may alternately be referred to as the divergence angle of light. Also, the "light emission angle" may alternately be referred to as the viewing angle. Light L10 output by the first light emission element LL10 toward the subject SBJ may be referred to as the "first incident light", and light L20 output by the second light emission element LL20 toward the subject SBJ may be referred to as the "second incident light". The first light emission angle $\theta1$ is an angle indicating a degree of divergence of the first incident light L10 from the first light emission element LL10, and the second light emission angle $\theta2$ is an angle indicating a degree of divergence of the second incident light L20 from the second light emission element LL20. The structures of the first and second light emission elements LL10 and LL20 will be described later with reference to FIGS. 3 to 5.

The biological signal measurement unit M10 may further include a photodetector (photodetecting portion) DT10 to detect light L50' that is output by the light emission portion LT10 toward the subject SBJ and modulated, for example, reflected or scattered, by the subject SBJ. The light L50' may be referred to as the modulated light or the light signal. The photodetector DT10 may be arranged adjacent to the light emission portion LT10 and may include at least one light receiving device. For example, a photodiode, a phototransistor, or a charge-coupled device (CCD) may be used as the light receiving device. A distance between the photodetector DT10 and the light emission portion LT10 may be within, for example, several millimeters, or in some cases, about 10 mm or more.

Figure 2:
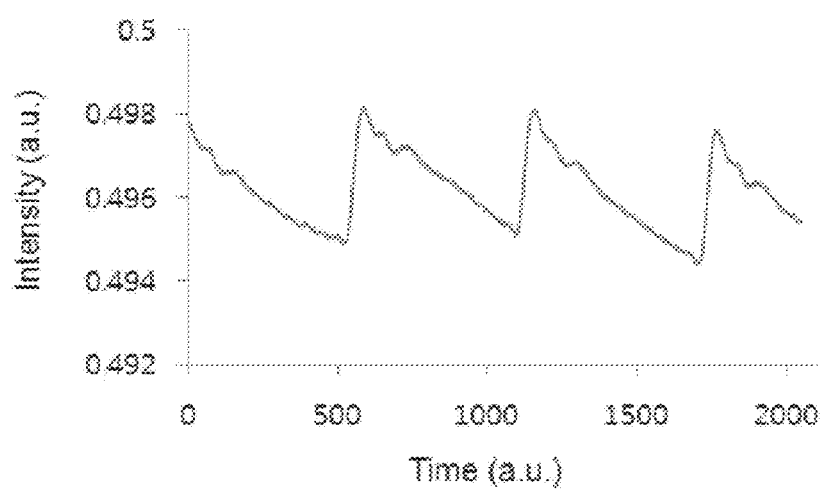
FIG. 2 is a graph showing an example of a surface pulse wave signal measured by a biological signal measurement unit, according to an exemplary embodiment.

A biological signal of the subject SBJ, measured by the biological signal measurement unit M10 may be, for example, a surface pulse wave. The surface pulse wave may be a waveform (signal) corresponding to a degree of trembling of a surface (skin surface) of the subject SBJ due to the contraction and relaxation of a blood vessel (BV1). The surface pulse wave corresponding to the trembling of the surface S1 may be measured by detecting the light L50' modulated on the surface S1 of the subject SBJ. The surface pulse wave may be referred to as the "skin surface pulse wave". FIG. 2 is a graph showing an example of a surface pulse wave signal measured by the biological signal measurement unit M10, according to an exemplary embodiment. The graph of FIG. 2 shows an exemplary result of measurement of a biological signal of the subject SBJ using only the first light emission element LL10 of the first and second light emission elements LL10 and LL20. A biological signal of the subject SBJ measured by the biological signal measurement unit M10 may be a signal other than a surface pulse wave. For example, the biological signal may be a photoplethysmogram (PPG) or other signal. Any biological signal that is measurable by a non-invasive method using light may be a subject of measurement.

Data measured by the biological signal measurement unit M10 may be transferred to the processor P10. The data processor of the processor P10 may perform the function of extracting and analyzing biological information of the subject SBJ from the data. For example, various pieces of biological information of the subject SBJ, such as, a systolic blood pressure, a diastolic blood pressure, a heart rate, a blood oxygen saturation, a blood vessel elasticity, a blood flow rate, or arterial stiffness, may be extracted and analyzed from the surface pulse wave signal shown in FIG. 2. As illustrated in FIG. 2, various signal parameters such as a peak, a dicrotic notch, a number of signals per unit time, an augmentation index (AI), a reflective wave transit time (RWTT), a subendocardial viability ratio (SEVR), or an ejection duration, may be extracted from the surface pulse wave signal and analyzed (that is, using pulse wave analysis (PWA)), thereby obtaining various pieces of biological information. Also, according to the present exemplary embodiment, the data processor may be configured to select a signal having a relatively high signal-to-noise ratio (SNR) from a plurality of detected signals measured by the light emission elements LL10 and LL20, and to extract and analyze biological information of the subject SBJ using the selected signal. Accordingly, the accuracy and reliability of the measurement may be improved.

Figure 3:
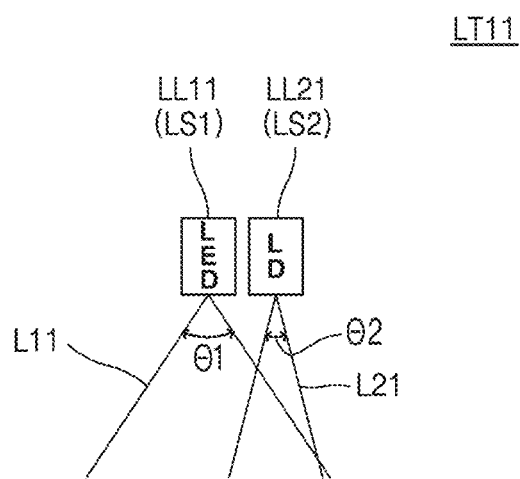
FIG. 3 illustrates a light emission portion for use with the biological signal measurement unit, according to an exemplary embodiment.

The first and second light emission elements LL10 and LL20 forming the light emission portion LT10 of FIG. 1 may include different types of light sources having different light emission angles, and examples thereof are illustrated in FIG. 3.

Referring to FIG. 3, a light emission portion LT11 may include a first light emission element LL11 and a second light emission element LL21. The first light emission element LL11 may include a first light source LS1, and the second light emission element LL21 may include a second light source LS2. The first light source LS1 may be the first light emission element LL11, and the second light source LS2 may be the second light emission element LL21. A type of the first light source LS1 may be different from that of the second light source LS2. In a detailed example, the first light source LS1 may be a light emitting diode (LED), and the second light source LS2 may be a laser diode (LD). In this case, a light emission angle $\theta1$ of the first light source LS1 may be, for example, about 80° to 180°, about 100° to 170°, or about 120° to 170°. A light emission angle $\theta2$ of the second light source LS2 may be, for example, about 0° to 90°, about 5° to 50°, or about 10° to 30°. Light L11 and light L21 are generated by the first light emission element LL11 and the second light emission element LL21, respectively.

Figure 4:
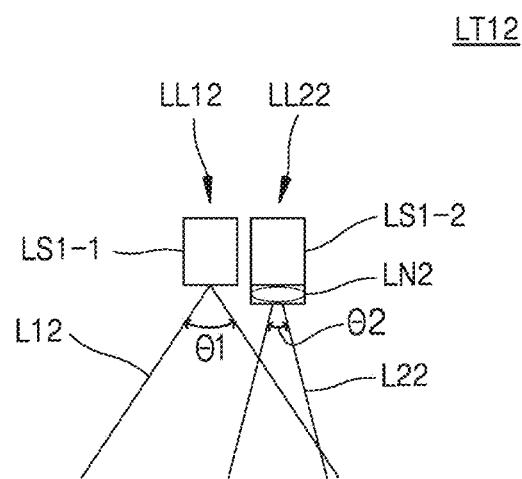
FIG. 4 illustrates a light emission portion for use with the biological signal measurement unit, according to another exemplary embodiment.

According to another exemplary embodiment, the first and second light emission elements LL10 and LL20 forming the light emission portion LT10 of FIG. 1 may include the same type of light source. For example both the first and section light emission elements LL10 and LL20 may be LDs, or both may be LEDs. In this case, either one of the two light emission elements LL10 and LL20 may further include an optical element (optical device) to adjust the light emission angle. The optical element may include at least one of, for example, a lens, an optical waveguide, a slit, a concave mirror, and a convex mirror. FIG. 4 illustrates an example in which a lens structure is employed as the optical element.

Referring to FIG. 4, a light emission portion LT12 may include a first light emission element LL12 and a second light emission element LL22. The first light emission element LL12 may include a first light source LS1-1, and the second light emission element LL22 may include a second light source LS1-2 that is the same type of light source as the first light source LS1-1. Both of the first light source LS1-1 and the second light source LS1-2 may be LEDs or LDs. Either of the first and second light emission elements LL12 and LL22, for example, the second light emission element LL22, may further include a lens structure LN2 to condense or disperse light generated by the light source corresponding thereto, that is, the second light source LS1-2. The lens structure LN2 may include at least one lens and generally have a positive (+) refractive power or a negative (−) refractive power. A lens may be omitted from the other one of the first and second light emission elements LL12 and LL22, for example, the first light emission element LL12. In other words, while the first light source LS1-1 may be used without a lens, the second light source LS1-2 that is the same type of the first light source LS1-1 may be used with the lens structure LN2. Accordingly, first light emission element LL12 and the second light emission element LL22 may have different light emission angles $\theta1$ and $\theta2$. Although the second light source LS1-2 and the lens structure LN2 are illustrated as being in contact with each other, they may be spaced apart from each other by a predetermined interval. Light L12 and light L22 are generated by the first light emission element LL12 and the second light emission element LL22, respectively.

Figure 5:
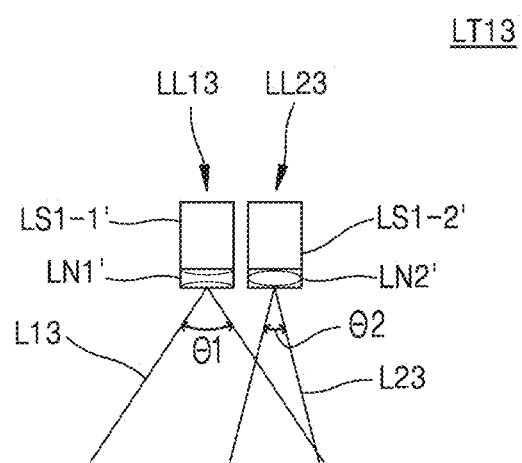
FIG. 5 illustrates a light emission portion for use with the biological signal measurement unit, according to another exemplary embodiment.

According to another exemplary embodiment, the first light emission element LL12 of FIG. 4 may include a lens structure, and an example thereof is illustrated in FIG. 5.

Referring to FIG. 5, a light emission portion LT13 may include a first light emission element LL13 and a second light emission element LL23. The first light emission element LL13 may include a first light source LS1-1', and the second light emission element LL23 may include a second light source LS1-2' that is the same type of light source as the first light source LS1-1'. The first light emission element LL13 may further include a first lens structure LN1' to condense or disperse light generated by the first light source LS1-1'. The second light emission element LL23 may further include a second lens structure LN2' to condense or disperse light generated by the second light source LS1-2'. The first lens structure LN1' and the second lens structure LN2' may have opposite refractive powers. The signs of the refractive powers of the first lens structure LN1' and the second lens structure LN2' may be opposite to each other. For example, the first lens structure LN1' may have a negative (−) refractive power, and the second lens structure LN2' may have a positive (+) refractive power. Alternatively, the first and second lens structures LN1' and LN2' may have different refractive powers of the same sign. When different lens structures LN1' and LN2' are applied to the same type of the two light sources LS1-1' and LS1-2', the two light emission elements LL13 and LL23 including the above elements may have different light emission angles θ1 and θ2. Light L13 and light L23 are generated by the first light emission element LL13 and the second light emission element LL23, respectively.

As described above with reference to FIG. 4, an optical element, that is, the lens structure LN2 configured to adjust the light emission angle, may be provided in any one of the first light emission element LL12 and the second light emission element LL22, or as described above with reference to FIG. 5, a first optical element, that is, the first lens structure LN1', is provided in the first light emission element LL13, and a second optical element, that is, the second lens structure LN2', which is different from the first optical element LN1', may be provided in the second light emission element LL23. In addition to or in place of a lens structure as described above, an optical waveguide, a slit, a concave mirror, or a convex mirror may be used as the optical element, or a combination of two or more of a lens structure, an optical waveguide, a slit, a concave mirror, and a convex mirror may be used. Also, the optical element may be applied to at least one of the first light emission element LL11 and the second light emission element LL21 of FIG. 3.

In an exemplary embodiment, a biological signal of a subject may be measured using a plurality of light emission elements (light sources) having different light emission angles. In this way, optimal illumination intensity and an optimal light irradiation area may be ensured regardless of a distance between a biological signal measurement unit (sensor) and a measurement surface of a subject, which will be described with reference to FIGS. 6 and 7.

Figure 6:
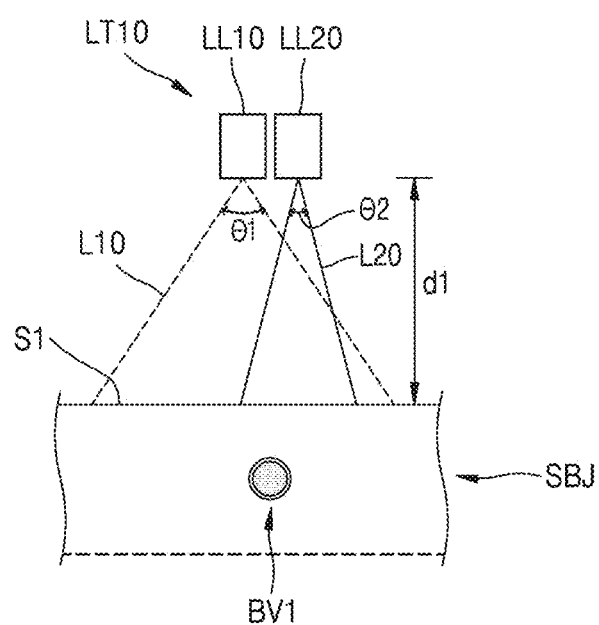
FIG. 6 illustrates light incident on a subject irradiated by the light emission portion when the light emission portion of the biological signal measurement unit is spaced apart, by a first distance, from a surface of the subject, according to an exemplary embodiment.

FIG. 6 illustrates light irradiated onto the subject SBJ by the light emission portion LT10 when the light emission portion LT10 of the biological signal measurement unit M10 is spaced apart from a surface (a measurement surface) S1 of the subject SBJ by a first distance d1, according to an exemplary embodiment. In the present exemplary embodiment. As compared with FIG. 7, the light emission portion (light source unit) LT10 of FIG. 6 is located relatively far from the measurement surface S1.

Referring to FIG. 6, when the light emission portion (light source unit) LT10 is located relatively far from the measurement surface S1, the second light emission element LL20 having a narrow light emission angle θ2, that is, a narrow viewing angle θ2, may be advantageous to secure optimal illumination intensity and an optimal light irradiation area for measurement of optimal biological signal.

Figure 7:
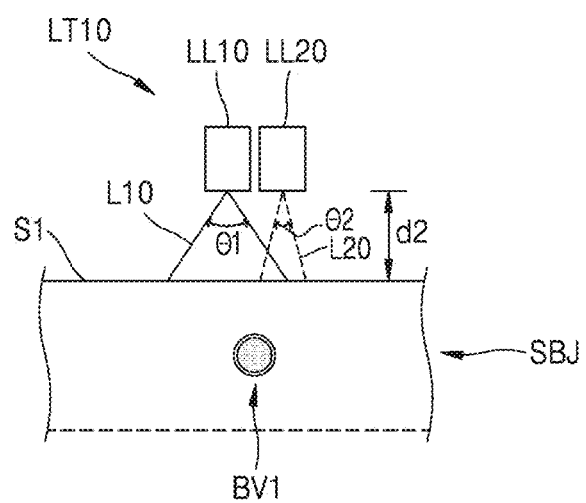
FIG. 7 illustrates light incident on a subject irradiated by the light emission portion when the light emission portion of the biological signal measurement unit is spaced apart, by a second distance, from the surface of the subject, according to another exemplary embodiment.

FIG. 7 illustrates light irradiated onto the subject SBJ by the light emission portion LT10 when the light emission portion LT10 of the biological signal measurement unit M10 is spaced apart from the measurement surface S1 of the subject SBJ by a second distance d2, according to an exemplary embodiment. In the present exemplary embodiment, as compared with FIG. 6, the light emission portion (light source unit) LT10 is located relatively close to the measurement surface S1.

Referring to FIG. 7, when the light emission portion (light source unit) LT10 is located relatively close to the measurement surface S1, the first light emission element LL10 having a wide light emission angle θ1, that is, a wide viewing angle θ1, may be advantageous to secure optimal illumination intensity and an optimal light irradiation area for measurement of optimal biological signal.

When measurement is performed using only one light source having a single light emission angle, because the light source is far away from or close to a measurement surface of the subject, the illumination intensity and the light irradiation area vary and may exceed optimal measurement conditions and thus the SNR of the thus obtained signal may be lowered. However, in the present exemplary embodiment, by using a plurality of emission elements (light sources) having different light emission angles, regardless of the distance between the measurement unit (biological signal measurement unit) and the measurement surface of the subject, an optimal illumination intensity and an optimal light irradiation area may be secured and thus a detected signal having a high SNR may be obtained.

Figure 8:
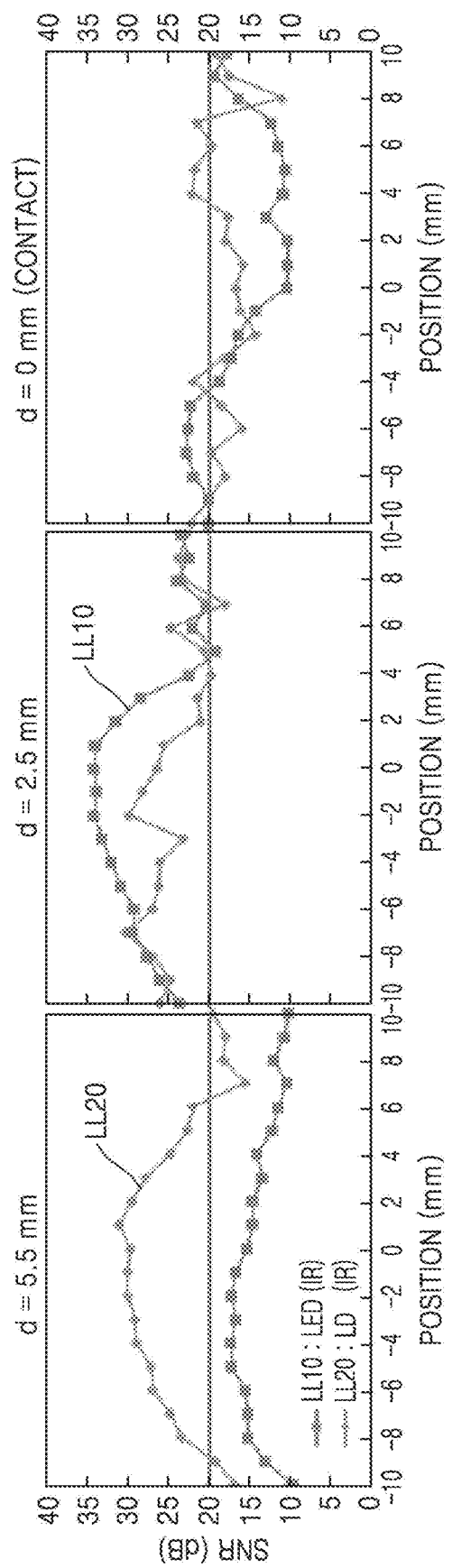
FIG. 8 is a graph showing a change of a signal-to-noise ratio (SNR) of a detected signal according to the height (i.e. a separation distance from a subject) of each of a plurality of light emission elements (light sources), according to an exemplary embodiment.

FIG. 8 is a graph showing a change of an SNR of a detected signal according to the height of each of the light emission elements (light sources), that is, a separation distance from the subject, according to an exemplary embodiment. The light emission portion LT10 used in the present exemplary embodiment may include an LED as the first light emission element LL10 and an LD as the second light emission element LL20. The light emission portion LT10 may correspond to the light emission portion LT11 of FIG. 3. In this case, both of the LED and the LD are infrared (IR) sources for generating IR light.

Referring to FIG. 8, when a distance d is 5.5 mm, it may be seen that a signal detected using light output by the second light emission element LL20, having a narrow light emission angle, has a relatively high SNR, which may correspond to the case described with reference to FIG. 6. Alternatively, when the distance d is 2.5 mm, it may be seen that a signal detected using light output by the first light emission element LL10, having a wide light emission angle, has a comparatively high SNR, which may correspond to the case described with reference to FIG. 7. Accordingly, when a distance between the measurement unit and the measurement surface of the subject is relatively long, that is, the distance d is large, a signal having a comparatively high SNR may be obtained by using the second light emission element LL20. When the distance between the measurement unit and the measurement surface of the subject is relatively short, that is, the distance d is small, a signal having a comparatively high SNR may be obtained by using the first light emission element LL10. Accordingly, a biological signal having superior quality may be measured regardless of the separation distance between the measurement unit and the measurement surface of the subject. As a result, accuracy and reliability in the measurement may be greatly improved. Based on FIG. 8 and experiment results similar thereto, when the distance d is equal to or greater than about 4.5 mm or about 4 mm, a signal detected using light output by the second light emission element LL20 may have a comparatively high SNR. Also, when the distance d is equal to or less than about 3.5 mm or about 4 mm, a signal detected using light output by the first light emission element LL10 may have a comparatively high SNR.

Alternatively, in FIG. 8, when the distance d is 0 mm, that is, the biological signal measurement unit and the measurement surface of the subject are in contact with each other, the trembling of a measurement surface, that is, a skin surface, may be limited by the biological signal measurement unit itself, and a low SNR may be measured using light output by both of the light emission elements LL10 and LL20. In this case, as illustrated in FIG. 9, a spacer SP1 may be used to prevent the biological signal measurement unit from contacting the measurement surface, that is, a skin surface.

Figure 9:
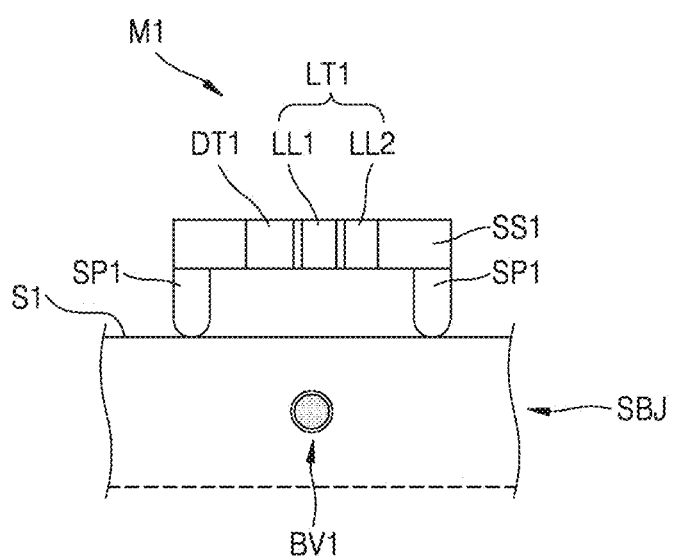
FIG. 9 illustrates a biological signal measurement unit for use with an apparatus for detecting biological information, according to another exemplary embodiment.

Referring to FIG. 9, a biological signal measurement unit M1 may be provided on a predetermined support SS1. The support SS1 may be a substrate. The substrate may be, for example, a printed circuit board (PCB) or a substrate similar thereto. The support SS1 may have a flexible or rigid structure. The biological signal measurement unit M1 may have a structure that is the same as or similar to that of the biological signal measurement unit M10 of FIG. 1. Accordingly, the biological signal measurement unit M1 may include a light emission portion LT1 having at least two light emission elements LL1 and LL2 having different light emission angles, and may further include a photodetector DT1. The photodetector DT1 may include at least one light receiving device. Also, according to the present exemplary embodiment, at least one spacer SP1, protruding to one side of the support SS1, may be provided. The light emission portion LT1 and the photodetector DT1 may be spaced apart from the measurement surface S1 of the subject SBJ by the spacer SP1. In other words, a minimum separation distance between the light emission portion LT1 and the photodetector DT1, and the measurement surface S1, may be secured by the spacer SP1. Accordingly, the problem of an SNR of a measured signal being reduced as the light emission portion LT1 and the photodetector DT1 contact the measurement surface S1 may be prevented. In the present exemplary embodiment, the biological signal measurement unit M1 may be considered to include all of the support SS1, the light emission portion LT1, the photodetector DT1, and the spacer SP1.

In FIG. 9, the use of the spacer SP1 is exemplary and another method may be used to achieve the purpose of forming the spacer SP1. Also, the forming position, structure, and number of the spacer SP1 are exemplary and may be changed in any of various ways. Also, in FIG. 9, the structure of the light emission portion LT1 and the photodetector DT1 being embedded in the support SS1 is exemplary, and the depth or position of embedding may be changed.

FIG. 9 exemplarily illustrates an apparatus for measuring an effective measurement surface of the subject SBJ using a non-contact method. When a biological signal such as a surface pulse wave of the subject SBJ is measured, a non-contact measurement method may be employed. However, when a photoplethysmogram (PPG) signal is detected, rather than a surface pulse wave, a contact measurement method may be employed instead of the non-contact measurement method. In this case, the spacer SP1 may be omitted, and a biological signal may be measured in a state in which the measurement unit M1 (LT1+DT1) is in contact with the effective measurement surface of the subject SBJ. Thus, the measurement method may be changed according to a biological signal to be measured.

Figure 10:
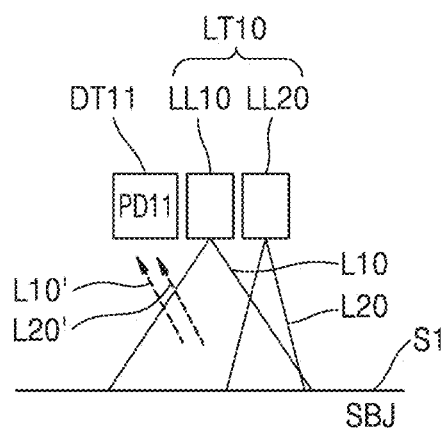
FIG. 10 illustrates a biological signal measurement unit for use with an apparatus for detecting biological information, according to another exemplary embodiment.

According to the present exemplary embodiment, the photodetector DT10 of FIG. 1 may include a light receiving device capable of receiving an optical signal from the first light emission element LL10 and an optical signal from the second light emission element LL20. Alternatively, the photodetector DT10 may include a first light receiving device that selectively receives the optical signal from the first light emission element LL10 and a second light receiving device that selectively receives the optical signal from the second light emission element LL20. FIG. 10 exemplarily illustrates the former and FIG. 11 exemplarily illustrates the latter.

Referring to FIG. 10, a photodetector DT11 may include a light receiving device PD11. The light receiving device PD11 may receive both of an optical signal (hereinafter, referred to as the first optical signal) L10' generated by the subject SBJ by incident light (hereinafter, referred to as the first incident light) L10 from the first light emission element LL10, and an optical signal (hereinafter, referred to as the second optical signal) L20' generated by the subject SBJ by incident light (hereinafter, referred to as the second incident light) L20 from the second light emission element LL20. In this case, the first optical signal L10' and the second optical signal L20' may be incident on the light receiving device PD11 at different times. By driving the first light emission element LL10 and the second light emission element LL20 at different timings, the first incident light L10 and the second incident light L20 may be irradiated onto the surface S1 of the subject SBJ with at different times. As a result, first optical signal L10' and the second optical signal L20' may be detected by the light receiving device PD11 at different times. In this case, a plurality of signals detected by a plurality of light emission elements LL10 and LL20 may be divided using a time-division method.

Figure 11:
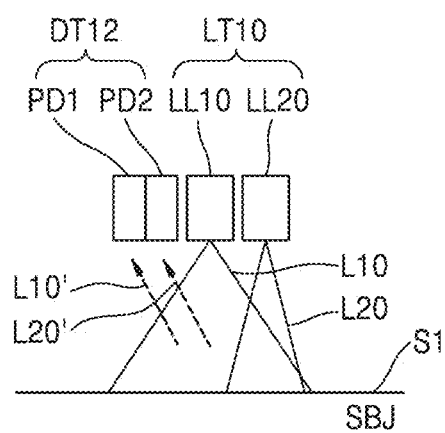
FIG. 11 illustrates a biological signal measurement unit for use with an apparatus for detecting biological information, according to another exemplary embodiment.

Referring to FIG. 11, a photodetector DT12 may include a first light receiving device PD1 and a second light receiving device PD2. The first light receiving device PD1 may be configured to selectively receive a first optical signal L10' generated in the subject SBJ from the first incident light L10 of the first light emission element LL10. The second light receiving de vice PD2 may be configured to selectively receive a second optical signal L20' generated in the subject SBJ from the second incident light L20 of the second light emission element LL20. In this case, the first incident light L10 and the second incident light L20 may fall within different wavelength ranges. The first optical signal L10' may fall within a wavelength range corresponding to the first incident light L10, and the second optical signal L20' may fall within a wavelength range corresponding to the second incident light L20. In a detailed example, the first incident light L10 and the first optical signal L10' may fall within a wavelength range corresponding to any one of regions of red R, green G, blue B, and infrared IR light. The second incident light L20 and the second optical signal L20' may fall within a wavelength range corresponding to another of the regions of red R, green G, blue B, and infrared IR light. Each of the first and second light receiving devices PD1 and PD2 may include a device for filtering light of a particular wavelength range. The first light receiving device PD1 may selectively receive the first optical signal L10' and the second light receiving device PD2 may selectively receive the second optical signal L20', using their respective filtering devices. In the present exemplary embodiment, a plurality of signals detected by the light emission elements LL10 and LL20 may be divided using a wavelength-division method. In this case, unlike the above-described time-division method, the first and second light emission elements LL10 and LL20 may be driven simultaneously.

According to the present exemplary embodiment, the light emission portion may include two or more light emission elements (light sources), and the photodetector may include two or more light receiving devices. In the following description, referring to FIGS. 12 to 23, various plane structures (array structures) of the biological signal measurement unit are described.

Figure 12:
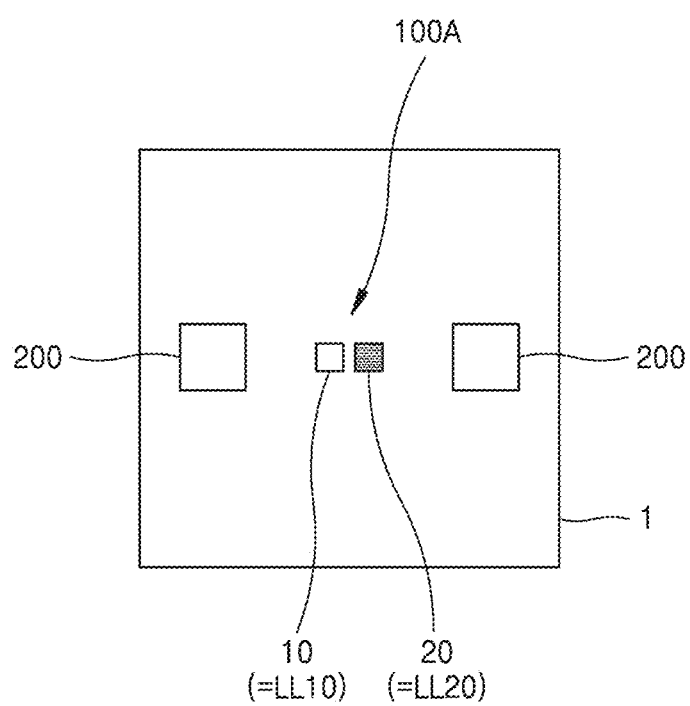
FIG. 12 is a plan view showing a structure of a biological signal measurement unit for use with an apparatus for detecting biological information, according to an exemplary embodiment.

FIG. 12 is a plan view showing a structure of a biological signal measurement unit for use with an apparatus for detecting biological information, according to an exemplary embodiment.

Referring to FIG. 12, a light emission portion 100A may include a first light emission element 10 and a second light emission element 20. The first light emission element 10 and the second light emission element 20 may correspond to the first light emission element LL10 and the second light emission element LL20 of FIG. 1, respectively. A plurality of light receiving devices 200 may be provided on the biological signal measurement unit around or near the light emission portion 100A. For example, two light receiving devices 200 may be provided, one at each of opposite sides of the light emission portion 100A. A plurality of light receiving devices 200 may constitute one photodetector. Each of the light receiving devices 200 may correspond to the light receiving device PD11 described in FIG. 10. Photodiodes, phototransistors, or charge-coupled devices (CCDs) may be used as the light receiving devices 200. The light emission portion 100A and the light receiving devices 200 may be provided on or in a substrate 1. The substrate 1 may be, for example, a PCB, or another substrate as would be understood by one of skill in the art. The substrate 1 may be a sort of support.

Figure 13:
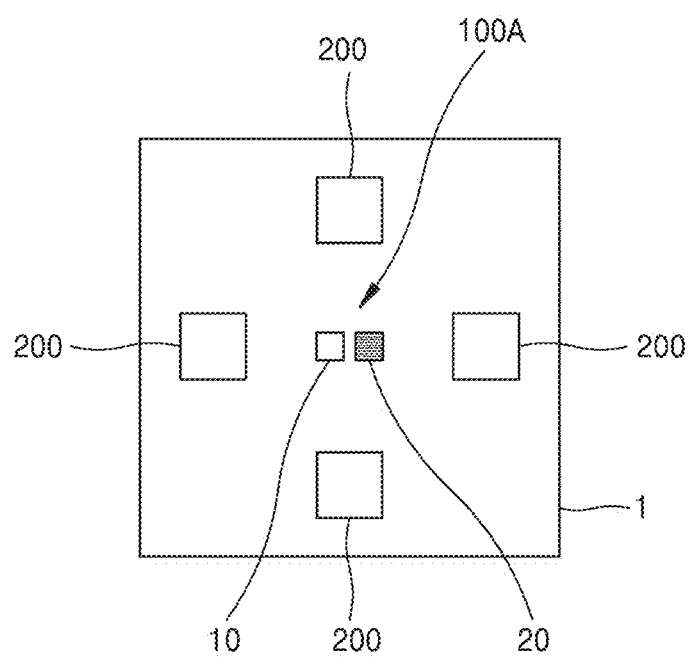
FIG. 13 is a plan view showing a structure of a biological signal measurement unit for use with an apparatus for detecting biological information, according to another exemplary embodiment.

Although FIG. 12 illustrates a case in which the light receiving devices 200 are provided at opposite sides of the light emission portion 100A, as illustrated in FIG. 13, four light receiving devices 200 may be provided, one at each of the upper, lower, left, and right sides of the light emission portion 100A. In other words, the light receiving devices 200 may be arranged in at least four positions around the light emission portion 100A.

Figure 14:
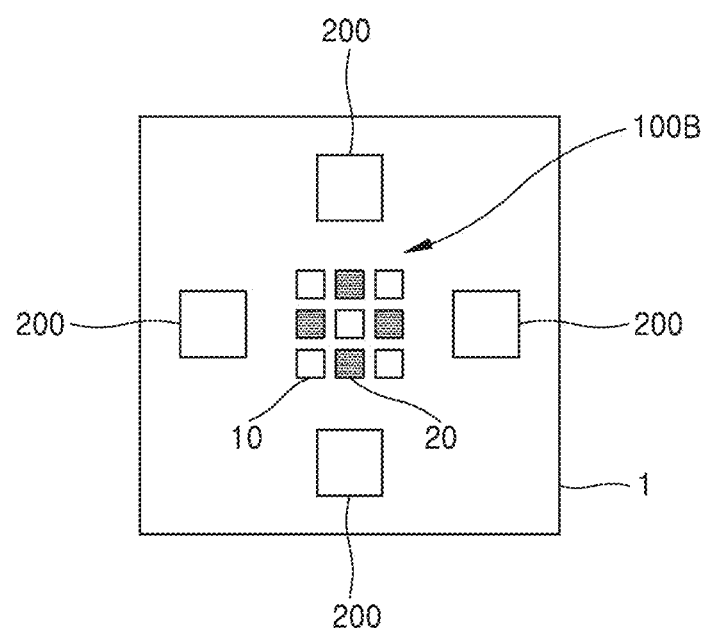
FIG. 14 is a plan view showing a structure of a biological signal measurement unit for use with an apparatus for detecting biological information, according to another exemplary embodiment.

In FIGS. 12 and 13, the light emission portion 100A may include a plurality of first light emission elements 10 and a plurality of second light emission elements 20, and FIG. 14 illustrates an example thereof. Referring to FIG. 14, a light emission portion 100B may include a two-dimensional (2D) array in which a plurality of first light emission elements 10 and a plurality of second light emission elements 20 are mixed.

Figure 15:
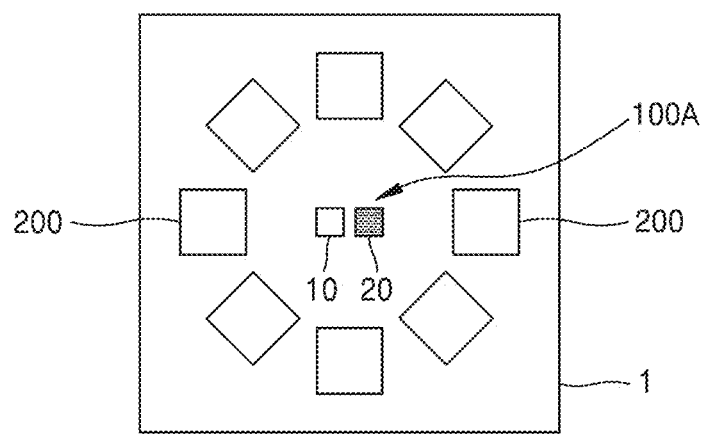
FIG. 15 is a plan view showing a structure of a biological signal measurement unit for use with an apparatus for detecting biological information, according to another exemplary embodiment.
Figure 16:
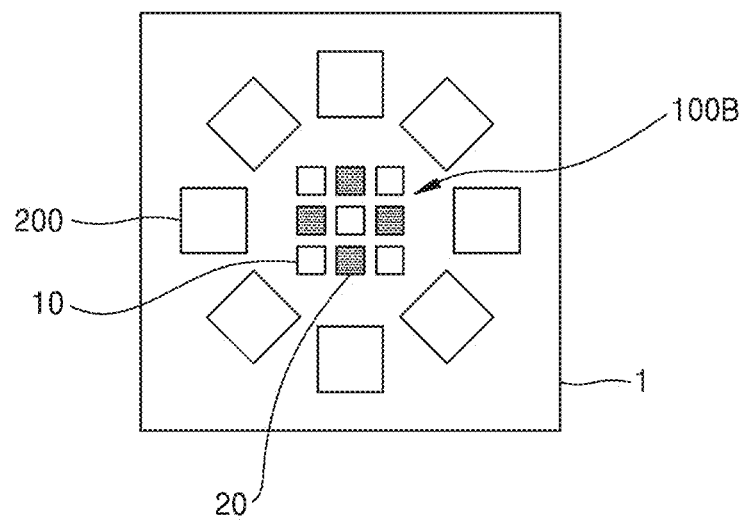
FIG. 16 is a plan view showing a structure of a biological signal measurement unit for use with an apparatus for detecting biological information, according to another exemplary embodiment.

Also, according to another exemplary embodiment, in the structures of FIGS. 12 to 14, a plurality of light receiving devices 200 may be arranged in an annular array around the light emission portions 100A and 100B, and FIGS. 15 and 16 illustrate examples thereof.

Figure 17:
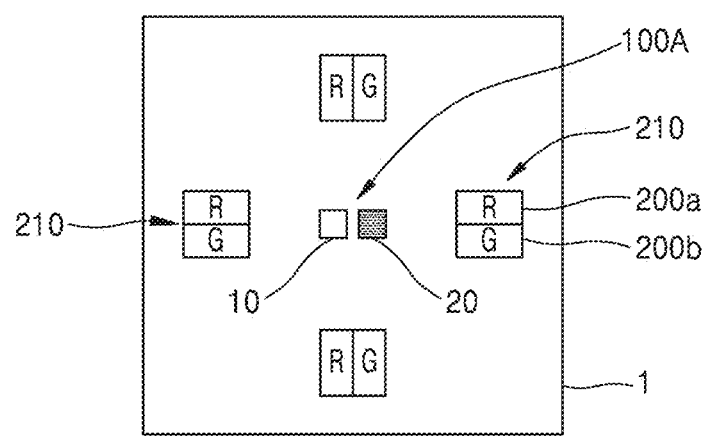
FIG. 17 is a plan view showing a structure of a biological signal measurement unit for use with an apparatus for detecting biological information, according to another exemplary embodiment.

FIG. 17 is a plan view showing a structure of a biological signal measurement unit for use with an apparatus for detecting biological information, according to another exemplary embodiment.

Referring to FIG. 17, the light emission portion 100A may include the first light emission element 10 and the second light emission element 20. A plurality of light receiving device regions 210 may be provided around the light emission portion 100A. Each of the light receiving device regions 210 may include a first light receiving device 200a and a second light receiving device 200b. The first light receiving device 200a may be a device receiving an optical signal from one of the first and second light emission elements 10 and 20. The second light receiving device 200b may be a device receiving an optical signal from the other of the first and second light emission elements 10 and 20. The first light receiving device 200a and the second light receiving device 200b may be configured to receive optical signals having different wavelength ranges. The first light receiving device 200a and the second light receiving device 200b may correspond to the first light receiving device PD1 and the second light receiving device PD2 of FIG. 11. In an example, the first light receiving device 200a may be a device receiving an optical signal in a red R region, and the second light receiving device 200b may be a device receiving an optical signal in a green G region. In this case, one of the first and second light emission elements 10 and 20 may be a red light source, and the other one may be a green light source. However, the light emission wavelengths of the first and second light emission elements 10 and 20 and the light receiving wavelengths of the first and second light receiving devices 200a and 200b are not limited to these specific wavelengths, and may be changed in various ways.

Figure 18:
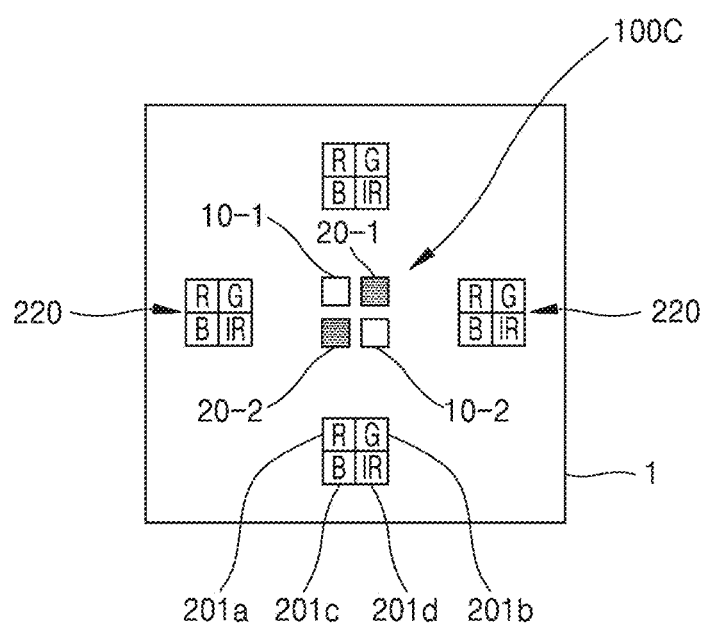
FIG. 18 is a plan view showing a structure of a biological signal measurement unit for use with an apparatus for detecting biological information, according to another exemplary embodiment.

The structure of FIG. 17 may be modified in a way as illustrated in FIG. 18. Referring to FIG. 18, a light emission portion 100C may include a plurality of first light emission elements 10-1 and 10-2 and a plurality of second light emission elements 20-2 and 20-2. The first light emission elements 10-1 and 10-2 may include a (1-1)th light emission element 10-1 and a (1-2)th light emission element 10-2. The (1-1)th light emission element 10-1 and the (1-2)th light emission element 10-2 may generate light of different wavelength ranges. A plurality of second light emission elements 20-1 and 20-2 may include a (2-1)th light emission element 20-1 and a (2-2)th light emission element 20-2. The (2-1)th light emission element 20-1 and the (2-2)th light emission element 20-2 may generate light of different wavelength ranges. A plurality of light receiving device regions 220 may be provided around the light emission portion 100C. Each of the light receiving device regions 220 may include first through fourth light receiving devices 201a to 201d. The first through fourth light receiving devices 201a to 201d may be configured to receive optical signals of different wavelength ranges. For example, the first through fourth light receiving devices 201a to 201d may be configured to receive optical signals in wavelength ranges of red R, green G, blue B, and infrared IR light. The light emission wavelengths of the light emission elements 10-1, 10-2, 20-2, and 20-2 may be determined in order to correspond with the wavelength ranges of the received optical signals.

Figure 19:
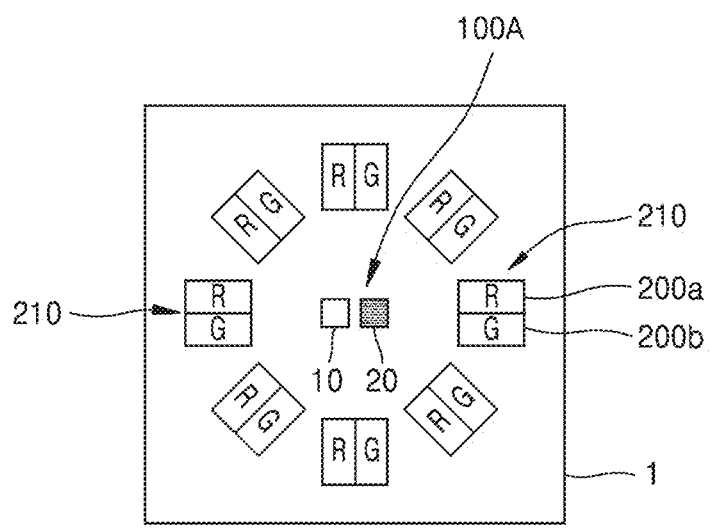
FIG. 19 is a plan view showing a structure of a biological signal measurement unit for use with an apparatus for detecting biological information, according to another exemplary embodiment.
Figure 20:
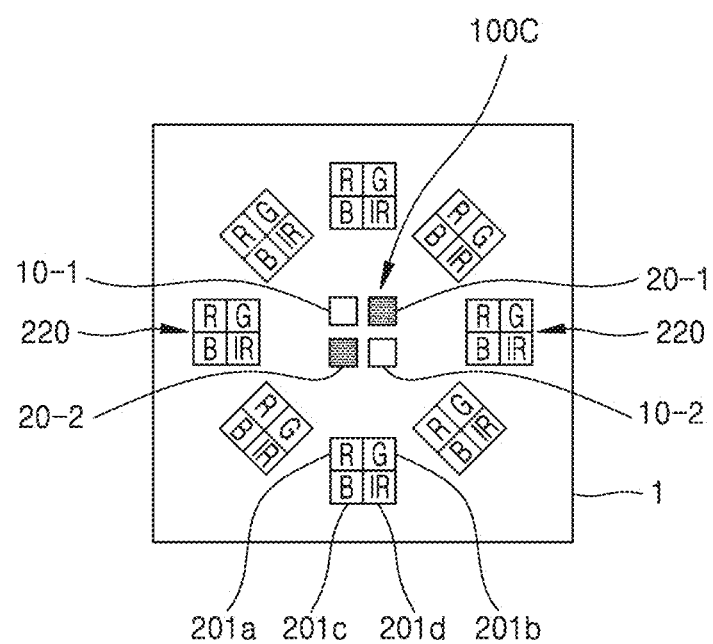
FIG. 20 is a plan view showing a structure of a biological signal measurement unit for use with an apparatus for detecting biological information, according to another exemplary embodiment.

In FIGS. 17 and 18, the light receiving device regions 210 and 220 may be arranged in an annular array around the light emission portions 100A and 100B, and FIGS. 19 and 20 illustrate examples thereof. The arrangement method of the R and G regions of the light receiving device region 210 of FIGS. 17 and 19, and the arrangement method of the R, G, B, and IR regions of the light receiving device region 220 of FIGS. 18 and 20, are exemplary and may be altered.

Figure 21:
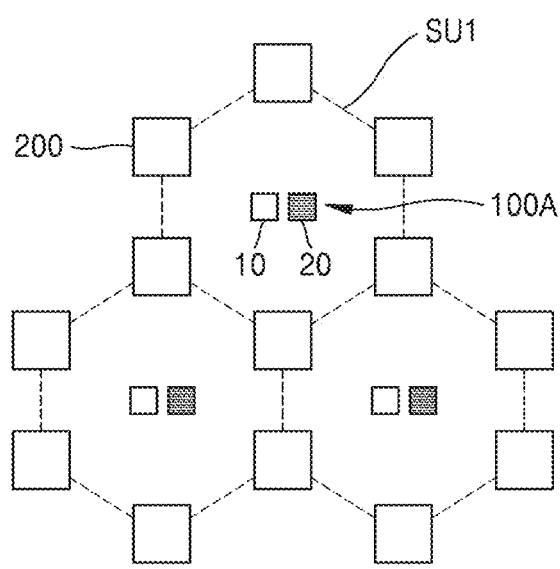
FIG. 21 is a plan view showing a structure of a biological signal measurement unit for use with an apparatus for detecting biological information, according to another exemplary embodiment.

FIG. 21 is a plan view showing a structure of a biological signal measurement unit for use with an apparatus for detecting biological information, according to another exemplary embodiment.

Referring to FIG. 21, the light emission portion 100A and the light receiving devices 200 arrayed around the light emission portion 100A form one sub-unit SU1. A plurality of sub-units SU1 may be repeatedly arranged. The light emission portion 100A may include at least one first light emission element 10 and at least one second light emission element 20. In each sub-unit SU1, the light receiving devices 200 may be arranged around the light emission portion 100A in a hexagonal array or in another shape. Two adjacent sub-units SU1 may share some of the light receiving devices 200. However, the structure of the sub-unit SU1 and the repetitive arrangement method of the sub-unit SU1 in FIG. 21 may be modified in various ways.

Figure 22:
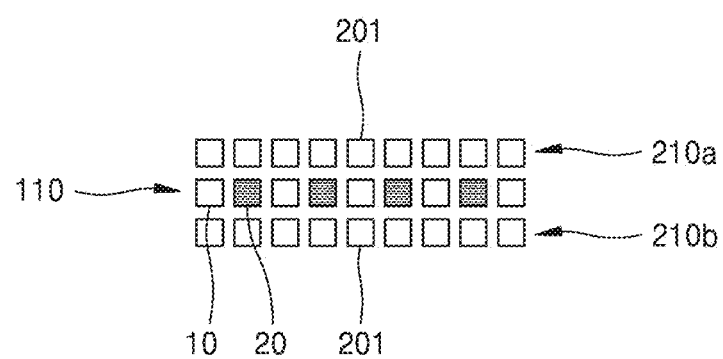
FIG. 22 is a plan view showing a structure of a biological signal measurement unit for use with an apparatus for detecting biological information, according to another exemplary embodiment.

FIG. 22 is a plan view of a structure of a biological signal measurement unit for use with an apparatus for detecting biological information, according to another exemplary embodiment.

Referring to FIG. 22, a light emission portion 110 may have a structure in which a plurality of first light emission elements 10 and a plurality of second light emission elements 20 are mixed in at least one line. The first light emission elements 10 and the second light emission elements 20 may be alternately arranged in a predetermined direction. A plurality of light receiving devices 201 may be provided around the light emission portion 110. The light receiving devices 201 may be arranged forming an array at at least one side of the light emission portion 110. For example, light receiving device arrays 210a and 210b, each including a plurality of the light receiving devices 201, may be provided at opposite sides of the light emission portion 110.

Figure 23:
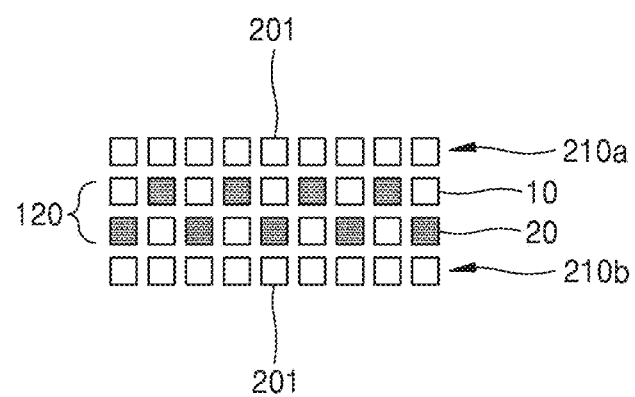
FIG. 23 is a plan view showing a structure of a biological signal measurement unit for use with an apparatus for detecting biological information, according to another exemplary embodiment.

The array structure of FIG. 22 may be changed in various ways. For example, although FIG. 22 illustrates that the first and second light emission elements 10 and 20 of the light emission portion 110 forming an array of a single line, an array of two or more lines may be formed, and FIG. 23 illustrates an example thereof. Referring to FIG. 23, a light emission portion 120 may have a structure in which a plurality of the first light emission elements 10 and a plurality of the second light emission elements 20 are mixed in an array forming two lines. The light receiving devices 201 may be arranged around and/or adjacent to the light emission portion 120 as shown in FIG. 23.

Figure 24:
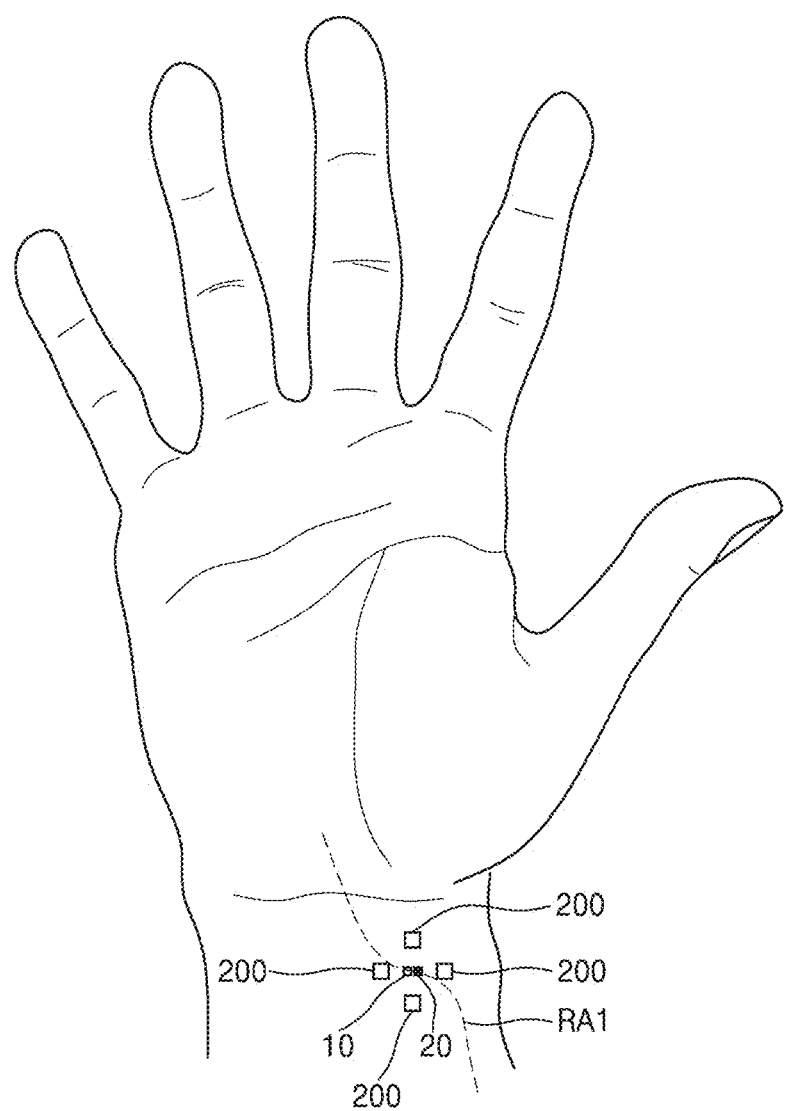
FIGS. 24 and 25 illustrate examples of cases in which a biological signal measurement unit is placed over a radial artery passing through a wrist of a subject and performs measurement, according to an exemplary embodiment.
Figure 25:
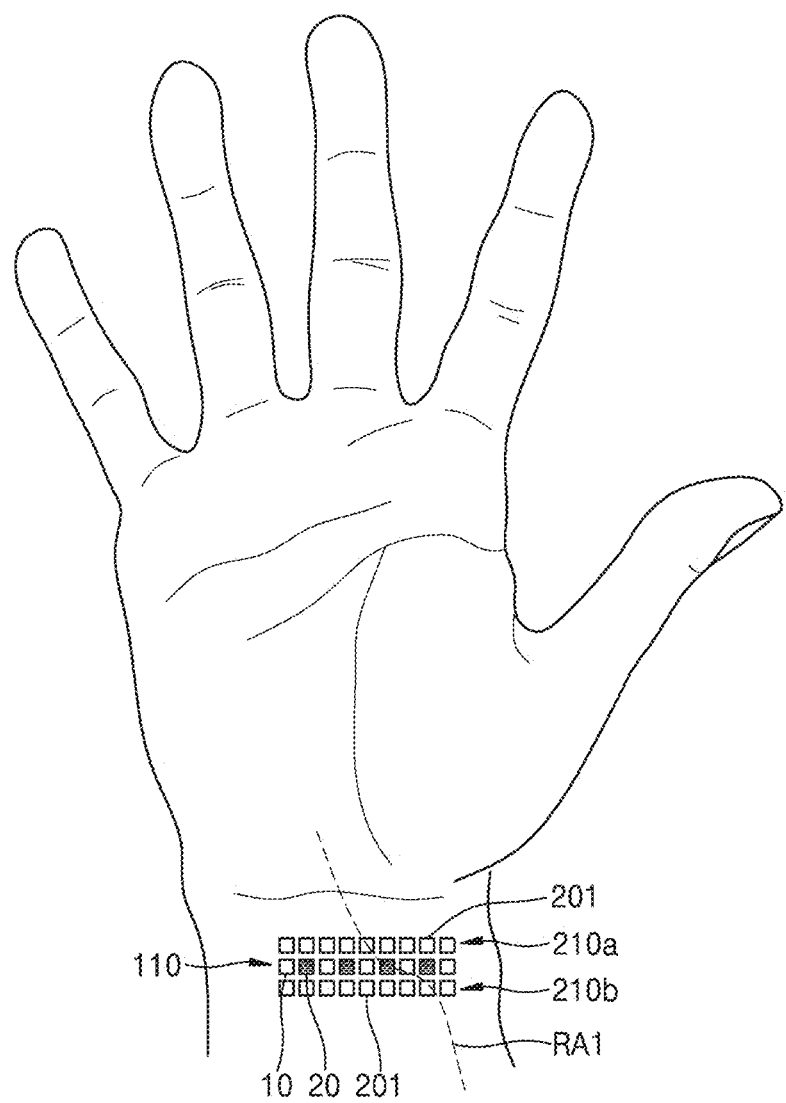

The biological signal measurement units having various structures described with reference to FIGS. 12 to 23 may be applied to the measurement area of a subject in various ways. The measurement area of a subject may be, for example, a specific portion of a human body. After the biological signal measurement unit is brought close to a specific portion of a human body, a biological signal may be measured. FIGS. 24 and 25 illustrate examples in which the biological signal measurement unit is placed over a radial artery RA1 passing through a wrist part of a subject and performs measurement, according to an exemplary embodiment. FIG. 24 illustrates a case of using the biological signal measurement unit corresponding to FIG. 13, and FIG. 25 illustrates a case of using the biological signal measurement unit corresponding to FIG. 22. However, the measurement positions illustrated in FIGS. 24 and 25 are exemplary and may be changed. For example, the measurement may be performed with respect to other parts of a subject such as a finger, a toe, an earlobe, etc., having a high blood vessel density in a human body, instead of the radial artery RA1.

The various plane structures (array structures) of the measurement unit described with reference to FIGS. 12 to 23 are exemplary and may be modified in various ways. Additionally, when a pair of a light-emitting device (light source) and a light receiving device corresponding thereto or a set of at least one light-emitting device and at least one light receiving device forms one measurement unit, a plurality of measurement units may be located at different areas of a subject. In this case, when a pulse wave signal is measured in different areas of an a subject using the measurement unit, a pulse transit time (PTT) may be obtained using a time difference between measured pulse wave signals and may be used for various biological information analyses.

Figure 26:
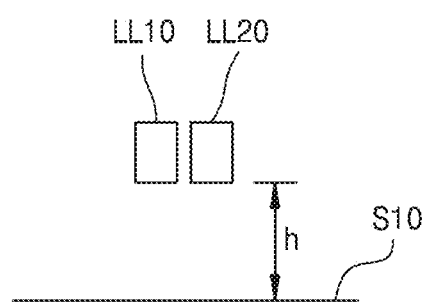
FIG. 26 illustrates a light emission portion for use with the biological signal measurement unit, according to another exemplary embodiment.
Figure 27:
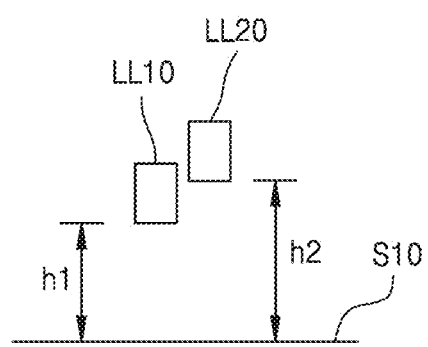
FIG. 27 illustrates a light emission portion for use with the biological signal measurement unit, according to another exemplary embodiment.

In the above-described biological signal measurement unit applied to the apparatus for detecting biological information, the first light emission element (first light source) (LL10) and the second light emission element (second light source) (LL20) may be located at the same height (distance) from a reference surface or at difference heights (distances). FIG. 26 illustrates a case in which the first light emission element LL10 and the second light emission element LL20 are located at the same height (distance) h from a reference surface S10. FIG. 27 illustrates a case in which the first light emission element LL10 and the second light emission element LL20 are located at different heights (distances) h1 and h2 from the reference surface S10.

Figure 28:
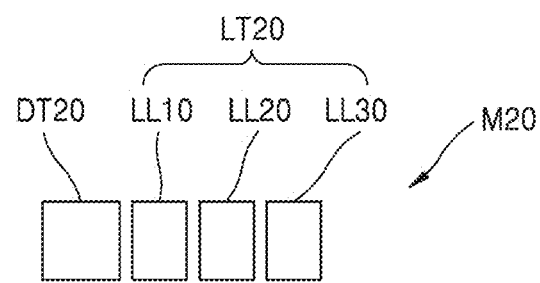
FIG. 28 illustrates a biological signal measurement unit for use with the apparatus for detecting biological information, according to another exemplary embodiment.

FIG. 28 illustrates a biological signal measurement unit M20 for use with the apparatus for detecting biological information, according to another exemplary embodiment.

Referring to FIG. 28, the biological signal measurement unit M20 may include a light emission portion LT20 and a photodetector DT20. The light emission portion LT20 may include at least three light emission elements LL10, LL20, and LL30 having different light emission angles (viewing angles). The first light emission element LL10, the second light emission element LL20, and the third light emission element LL30 may have different light emission angles. The first light emission element LL10 and the second light emission element LL20 may correspond to the first light emission element LL10 and the second light emission element LL20 of FIG. 1, respectively. The third light emission element LL30 may have a light emission angle different from that of the first and second light emission elements LL10 and LL20. In a detailed example, the first light emission element LL10 may include a first LED, the second light emission element LL20 may include a first LD, and the third light emission element LL30 may include a second LED or a second LD. In this case, the second LED (or second LD) may have a light emission angle different from that of the first LED (or first LD). At least one of the first through third light emission elements LL10, LL20, and LL30 may include an optical element to adjust the light emission angle similar to the one described with reference to FIGS. 4 and 5. Alternatively, although only one photodetector DT20 is illustrated at one side of the light emission portion LT20, a plurality of photodetectors DT20 may be provided around the light emission portion LT20. When three or more light emission elements LL10, LL20, LL30, having different light emission angles (viewing angles), are used as in the present exemplary embodiment, the accuracy and reliability of the measurement may be further improved.

Figure 29:
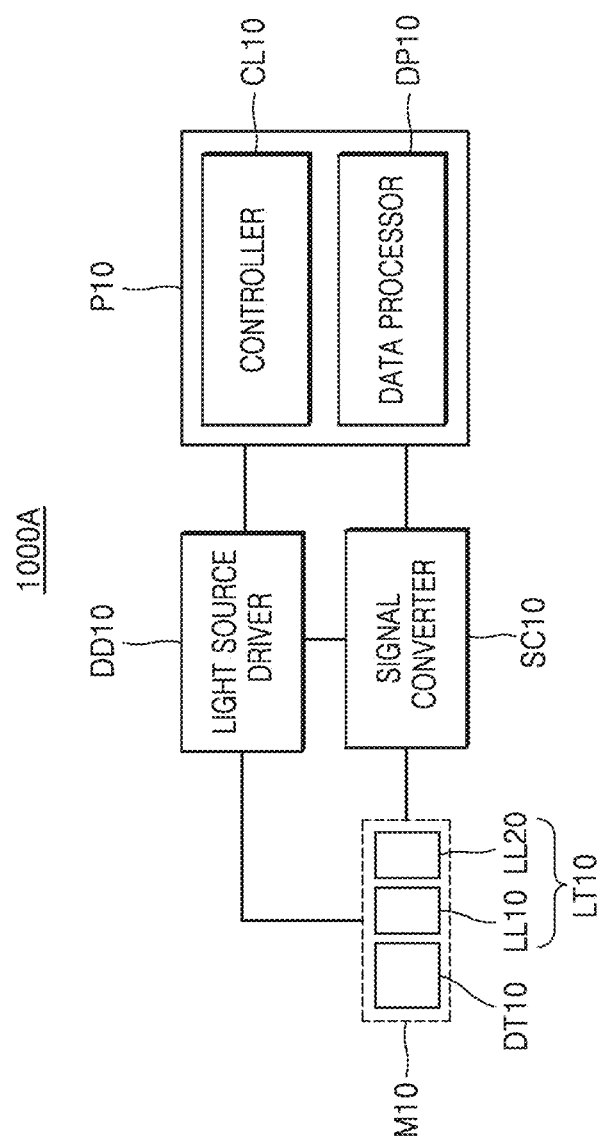
FIG. 29 is a block diagram showing a structure of the apparatus for detecting biological information of FIG. 1, according to an exemplary embodiment.

FIG. 29 is a block diagram showing a structure of the biological information detection apparatus 1000 of FIG. 1, according to an exemplary embodiment.

Referring to FIG. 29, a biological information detection apparatus 1000A may include the biological signal measurement unit M10. The biological signal measurement unit M10 may have the structure of the biological signal measurement unit M10 of FIG. 1 or may be modified according to any other various structures in view of the above descriptions. The biological information detection apparatus 1000A may include a processor P10 including a data processor DP10 that extracts and analyzes biological information of a subject from the data measured by the biological signal measurement unit M10. The processor P10 may include a controller CL10 for controlling an overall operation of the biological information detection apparatus 1000A.

The biological information detection apparatus 1000A may include a light source driver DD10 connected to the biological signal measurement unit M10. The light source driver DD10 may drive or control a plurality of light emission elements LL10 and LL20 of the light emission portion LT10. The light source driver DD10 may be connected to the processor P10. The biological information detection apparatus 1000A may include a signal converter SC10 that is connected between the biological signal measurement unit M10 and the processor P10. The signal converter SC10 may be connected to the light source driver DD10. The signal converter SC10 may include, for example, an analog front-end (AFE) circuit. The signal converter SC10 may convert an analog signal input by the measurement unit M10 to a digital signal and may transmit the digital signal to the data processor DP10 of the processor P10. The signal converter SC10 may include a signal amplifier, a noise filter, an analog-to-digital (AD) converter, etc. A detected signal measured by the measurement unit M10 may be amplified by the signal amplifier, removed of noise by the noise filter, and converted to a digital signal by the AD converter. A combination of the light source driver DD10 and the signal converter SC10 may be regarded as one driver and signal converter, which may correspond to the driver and signal converter DS10 of FIG. 1. The light source driver DD10 and the signal converter SC10 may be formed together in one chip (device) or may be formed separately.

The data processor DP10 may use an algorithm to select a signal having a high SNR and superior quality from among a plurality of detected signals measured by the light emission elements LL10 and LL20. The data processor DP10 may be configured to select a signal having a high SNR and superior quality using the algorithm. Also, the data processor DP10 may be configured to extract and analyze biological information of a subject using the selected signal or using the entire detected signals. For example, when the signal measured by the biological signal measurement unit M10 is the surface pulse wave signal of FIG. 2, various signal parameters such as a peak, a dicrotic notch, number of signals per unit time, an augmentation index (AI), a reflective wave transit time (RWTT), a subendocardial viability ratio (SEVR), or an ejection duration may be extracted from the surface pulse wave signal and analyzed (for example, using pulse wave analysis (PWA)), thereby obtaining various pieces of biological information of a subject, such as, a systolic blood pressure, a diastolic blood pressure, a heart rate, a blood oxygen saturation, a blood vessel elasticity, a blood flow rate, or arterial stiffness. Since a well-known algorithm may be used to extract various signal parameters from pulse wave signal by the data processor DP10, a detailed description thereof is omitted.

The controller CL10 of the processor P10 may control overall operations of the light source driver DD10, the signal converter SC10, and the data processor DP10. Although not illustrated, the processor P10 may further include data communication unit and/or memory. The data communication unit may transmit biological information obtained through the data processor DP10 to an external device. Also, the data communication unit may receive a predetermined input signal from the external device. The memory may store the information obtained by the data processor DP10, store a program for the data processor DP10 and the controller CL10, or store a user's command.

Figure 30:
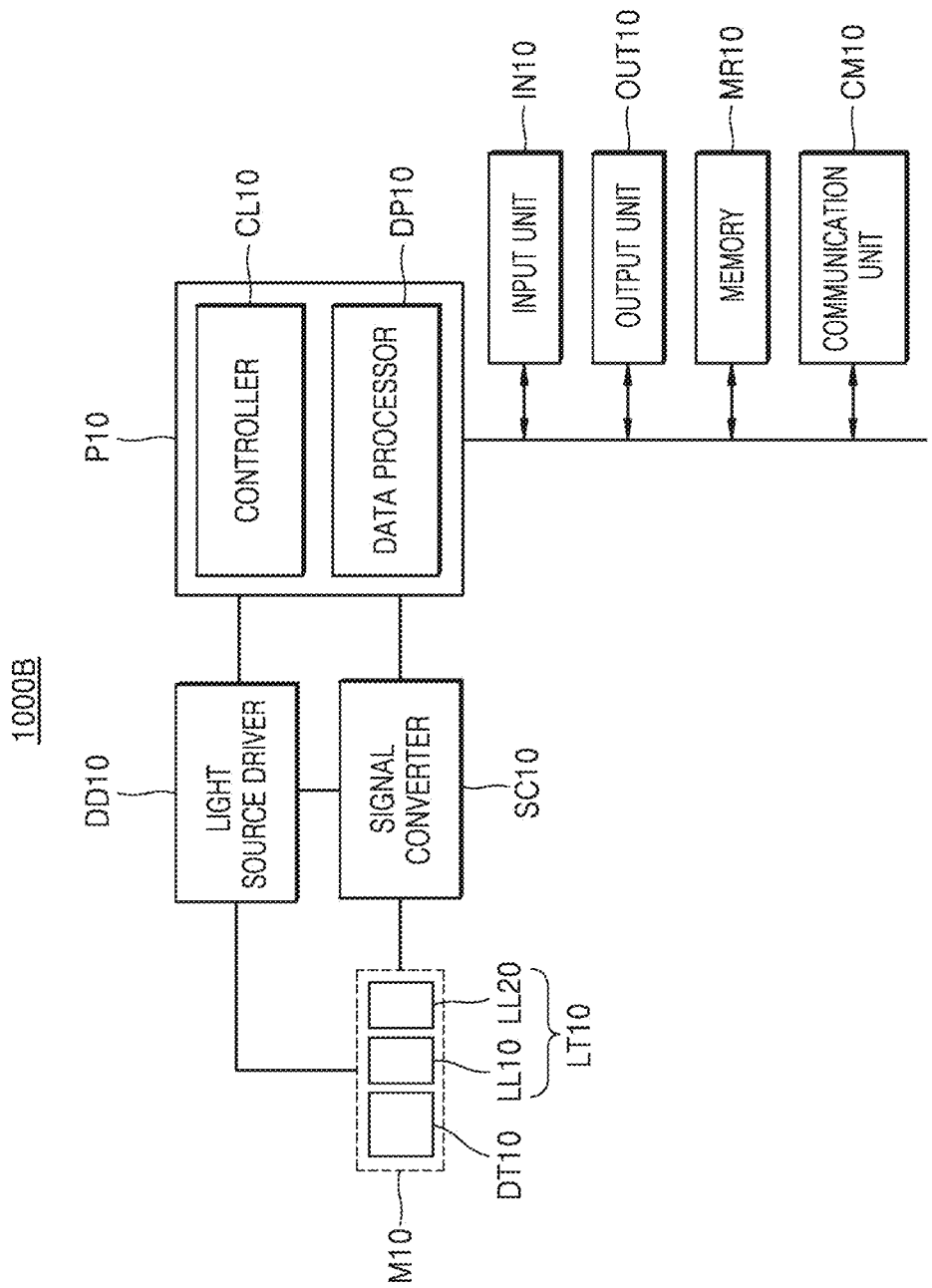
FIG. 30 is a block diagram showing a structure of the apparatus for detecting biological information of FIG. 1, according to another exemplary embodiment.

FIG. 30 is a block diagram showing a structure of a biological information detection apparatus 1000B, according to another exemplary embodiment.

Referring to FIG. 30, as described in FIG. 29, the biological information detection apparatus 1000B may include the biological signal measurement unit M10, the light source driver DD10, the signal converter SC10, and the processor P10. The biological information detection apparatus 1000B of the present exemplary embodiment may further include an input unit IN10, an output unit OUT10, a memory MR10, and a communication unit CM10, which are connected to the processor P10.

The input unit IN10 may be a device used by a user to input a command to the biological information detection apparatus 1000B and may be, for example, a keypad, a touch screen, a speech recognition device, or a button type input device. The output unit OUT10 is a device for outputting a result of analysis by the biological information detection apparatus 1000B and may be, for example, a display device, a sound system, a vibration device, or a printer. The input unit IN10 and the output unit OUT10 together may be referred to as the user interface. The user may be a target of which biological information is to be measured, that is, the subject, or a person who may use the biological information detection apparatus 1000B, for example, a medical expert, which may include a wider array of people than just the subject.

The memory MR10 may store a user's command and/or a result of analysis. Also, the memory MR10 may store a program for the data processor DP10 and the controller CL10. For example, the memory MR10 may include at least one of storage medium such as flash memory, a hard disc, a multimedia card (MMC), card type memory such as SD or XD memory, random access memory (RAM), static random access memory (SRAM), read-only memory (ROM), electrically erasable programmable read-only memory (EE-PROM), programmable read-only memory (PROM), magnetic memory, a magnetic disc, and an optical disc.

The communication unit CM10 may be configured to transmit the analyzed result (data) to other external device. The external device communicating with the communication unit CM10 may be, for example, a medical apparatus using analyzed biological information, or a printer that prints the result. The external device may be a smartphone (mobile phone), a personal digital assistant (PDA), a laptop computer, a personal computer (PC), and other mobile or non-mobile computing device, but is not limited thereto.

The communication unit CM10 may be connected to an external device by wire or wirelessly. For example, the communication unit CM10 may communicate with an external device by a communication method such as Bluetooth communication, Bluetooth low energy (BLE) communication, near field communication, wireless local area network (WLAN) (wireless LAN) communication, Zigbee communication, infrared data association (IrDA) communication, Wi-Fi direct (WFD) communication, ultra-wideband (UWB) communication, ANT/ANT+ communication, or Wi-Fi communication, but not limited thereto.

Figure 31:
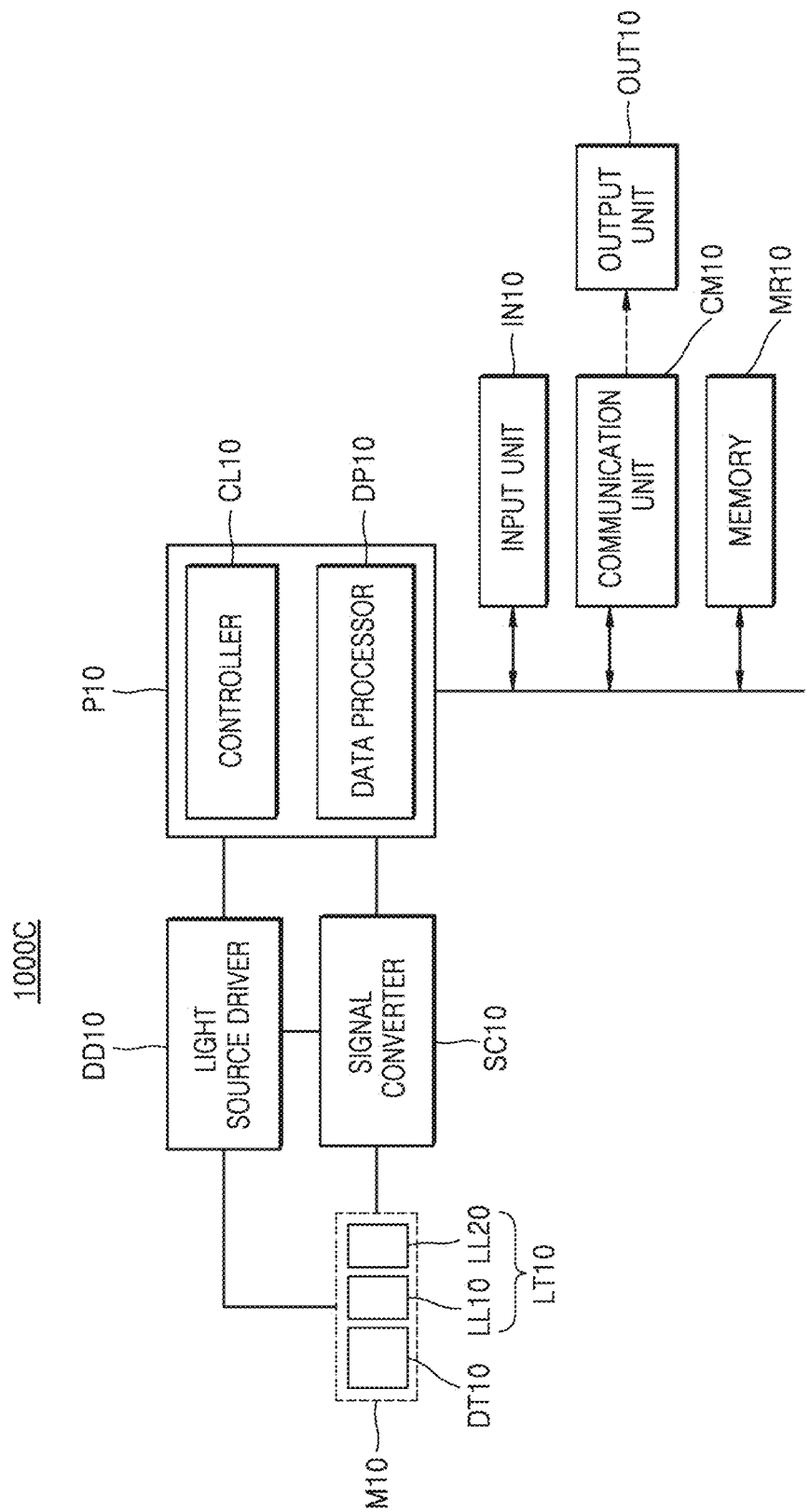
FIGS. 31 to 33 are block diagrams showing modified examples of the structure of FIG. 30.

In FIG. 30, the output unit OUT10 may be provided in a separate device outside the biological information detection apparatus 1000B, and FIG. 31 illustrates an example thereof. Referring to FIG. 31, the output unit OUT10 may be provided in another device separate from the biological information detection apparatus 1000C and may receive data (biological information) through communication with the communication unit CM10.

Figure 32:
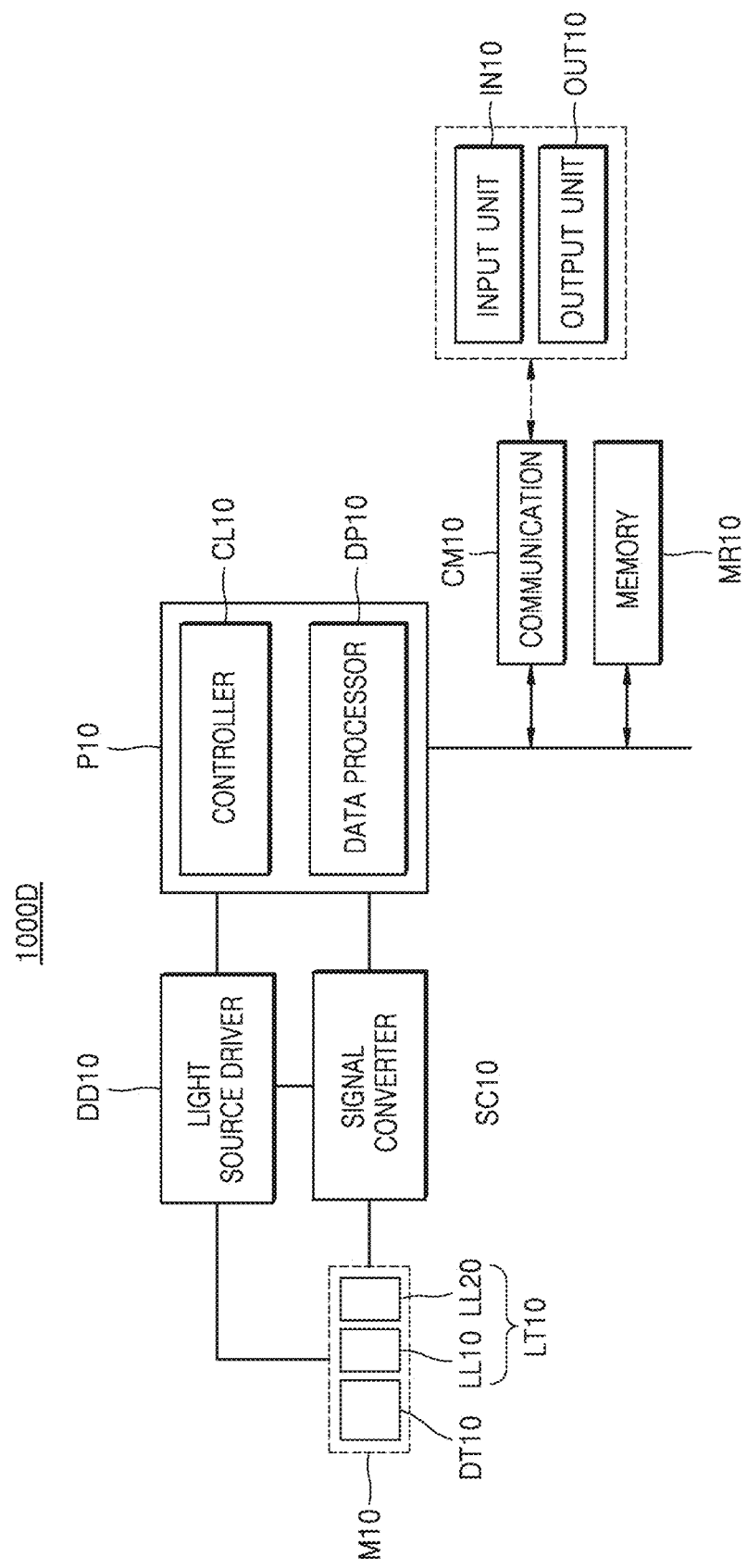

According to another exemplary embodiment, in FIG. 30, both of the input unit IN10 and the output unit OUT10 may be provided in separate devices outside the biological information detection apparatus 1000B and FIG. 32 illustrates an example thereof. Referring to FIG. 32, the input unit IN10 and the output unit OUT10 may be provided in a separate device outside a biological information detection apparatus 1000D, and may exchange input information and output information through data communication with the communication unit CM10.

Figure 33:
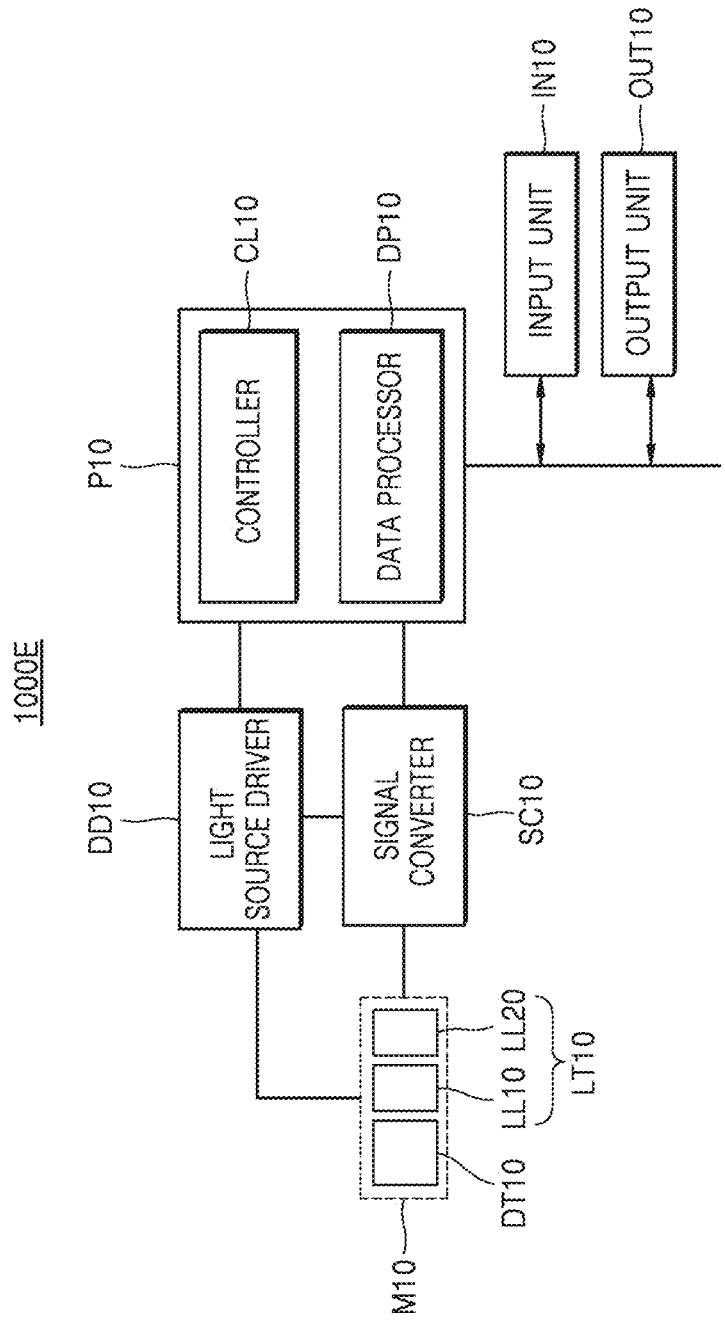

According to another exemplary embodiment, in FIG. 30, the memory MR10 and the communication unit CM10 may be provided inside the processor P10. In some cases, at least one of the memory MR10 and the communication unit CM10 may be omitted, and FIG. 33 illustrates an example thereof. Referring to FIG. 33, a biological information detection apparatus 1000E may include the input unit IN10 and the output unit OUT10, which are connected to the processor P10. Although not illustrated, the processor P10 may further include at least one of the memory MR10 and the communication unit CM10. The biological information detection apparatuses 1000A to 1000E described with reference to FIGS. 29 to 33 may be referred to as the biological information detection system. Also, in FIGS. 29 to 33, the processor P10 may be connected to the signal converter SC10 and/or the light source driver DD10 through wireless communication.

At least some of the above-described biological information detection apparatuses may form at least a part of a portable device or a wearable device. The portable device may be, for example, a mobile phone, and the wearable device may be, for example, a wristwatch type device, a wristband type device, or a bracelet type device, or may take any of various forms, such as glasses, a hairband, or a ring.

Figure 34:
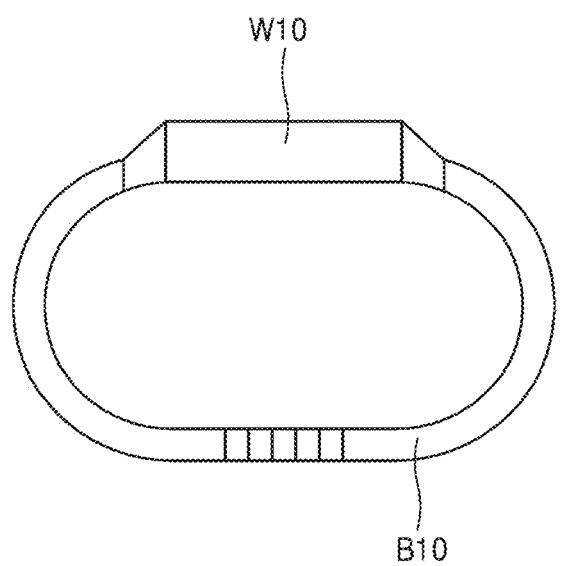
FIG. 34 illustrates an example of a wearable device for use with the apparatus for detecting biological information, according to an exemplary embodiment.

FIG. 34 illustrates an example of a wearable device in which the apparatus for detecting biological information is useable, according to an exemplary embodiment. In the present exemplary embodiment, the wearable device is a wristwatch type device.

Referring to FIG. 34, a wristwatch type device may include a device main body part (watch part) W10 and a band part B10. At least a part of an apparatus for detecting biological information according to the present exemplary embodiment may be disposed in the band part B10 or in the device main body part W10, or parts of the apparatus may be disposed in each of the band part B10 and the device main body part W10.

FIG. 35 illustrates an example of a portable device for use with the apparatus for detecting biological information, according to an exemplary embodiment. In the present exemplary embodiment, the portable device is a mobile phone.

In FIG. 35, the left image shows the front surface of a mobile phone and the right image shows a rear surface of the mobile phone. The measurement unit (biological signal measurement unit) of the apparatus for detecting biological information according to the present exemplary embodiment may be exposed in the front surface or rear surface of the mobile phone. Alternatively, the measurement unit may be exposed in a side surface (including an upper, lower, left, or right surface) of the mobile phone.

A part of the apparatus for detecting biological information according to another exemplary embodiment may be provided in the wearable device (wristwatch type device) of FIG. 34, and another part may be provided in the portable device (mobile phone) of FIG. 35. Also, the wearable device and the portable device may interact with each other and data communication may be performed therebetween.

The biological information detection apparatuses (or biological information detection systems) according to the present exemplary embodiments may be used not only with a portable device or a wearable device, as described with reference to FIGS. 34 and 35, but also may be used with or as medical equipment used in hospitals or health examination organizations, middle- or small-sized medical equipment provided in public organizations, and compact medical equipment and various health-care apparatuses that may be possessed by an individual.

In the following description, biological information detection methods according to exemplary embodiments will be described below.

Figure 36:
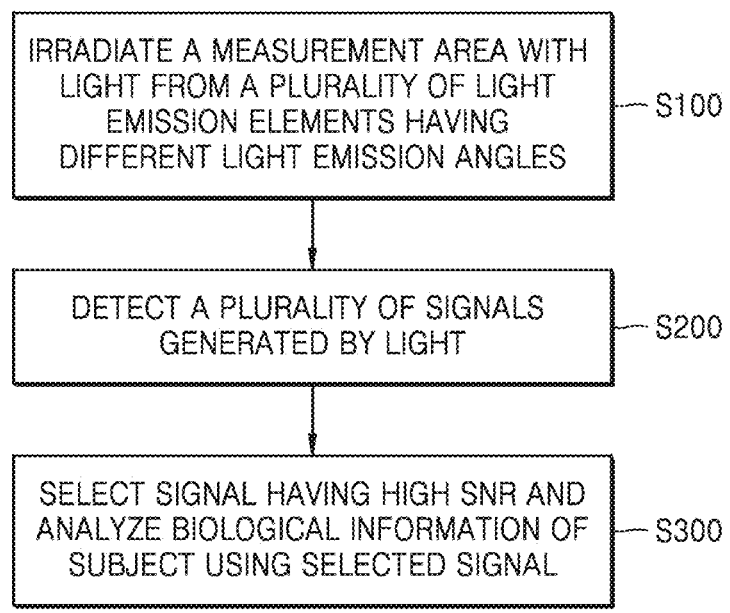
FIG. 36 is a flowchart explaining a method of detecting biological information, according to an exemplary embodiment.

FIG. 36 is a flowchart explaining a method of detecting biological information, according to an exemplary embodiment. The following description with reference to FIG. 36 is related to the biological information detection apparatus described with reference to FIGS. 1 to 35 and relevant descriptions thereof. Accordingly, the method of FIG. 36 may be understood based on the descriptions of FIGS. 1 to 35.

Referring to FIG. 36, the method of detecting biological information according to the present exemplary embodiment may include irradiating a measurement area of a subject with a plurality of lights (incident lights) having different light emission angles to using at least two light emission elements having different light emission angles (S100), detecting a plurality of signals generated by the plurality of lights being reflected by the measurement area (S200), and selecting a signal having a high SNR from among the detected signals and extracting and analyzing biological information of the subject using the selected signal (S300). In the operation S100, the at least two light emission elements having different light emission angles may correspond to, for example, the two light emission elements LL10 and LL20 of FIG. 1. The detection of signals in operation S200 may be performed by, for example, the photodetectors DT10, DT11, and DT12 of FIGS. 1, 10, and 11. The extraction and analysis of the biological information in the operation S300 may be performed by, for example, the data processor DP10 of FIGS. 1 and 29.

According to the present exemplary embodiment, in the operation S100, the measurement area of the subject may be irradiated with the lights at different times by driving the at least two light emission elements at different times. Likewise, in conjunction with the operation S100, in the operation S200, the signals may be detected at different times. The method may be summarized as shown in a flowchart of FIG. 37.

Figure 37:
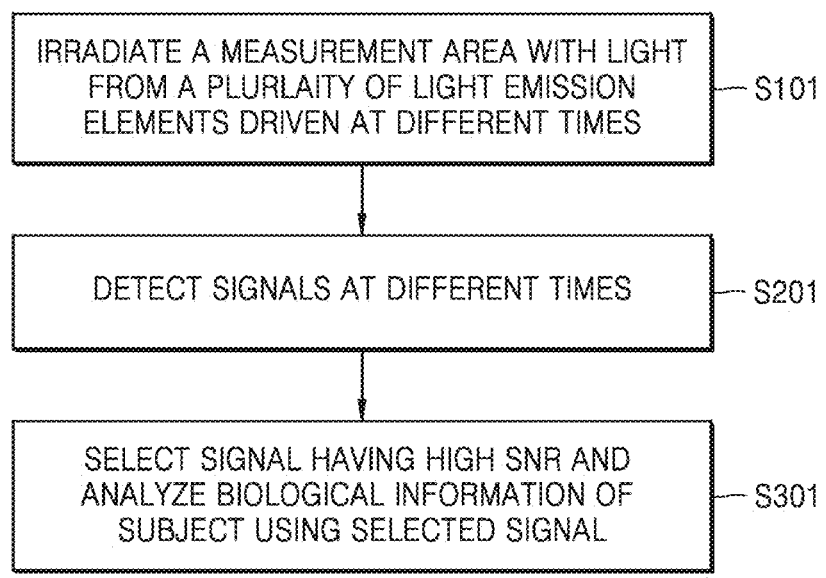
FIG. 37 is a flowchart explaining a method of detecting biological information, according to another exemplary embodiment.

Referring to FIG. 37, a method of detecting biological information according to the present exemplary embodiment may include irradiating a measurement area of a subject with a plurality of lights (incident lights) by driving at least two light emission elements at different times (S101), detecting, at different times, a plurality of signals generated by the lights being reflected from the subject (S201), and selecting a signal having a high SNR from among the detected signals and extracting and analyzing biological information of the subject using the selected signal (S301).

Figure 38:
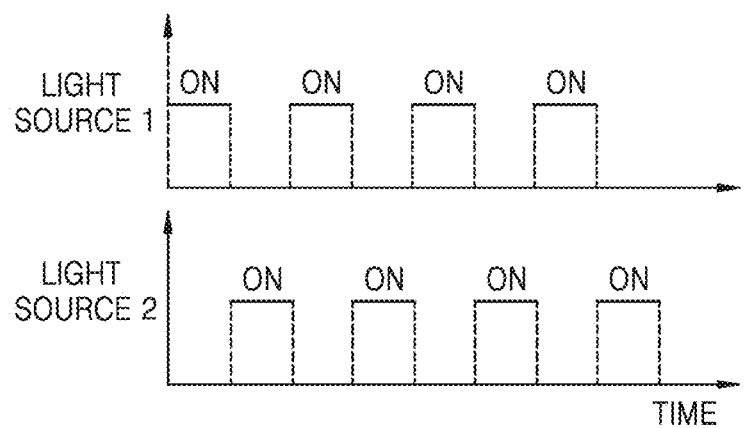
FIG. 38 is a graph explaining a method of detecting biological information, according to another exemplary embodiment.

When, as in the operation S101, two light emission elements are driven at different times, on and off (ON and OFF) operations of the two light emission elements (light sources) may be performed as illustrated in, for example, FIG. 38. Referring to FIG. 38, as time passes, a first light emission element (first light source) and a second light emission element (second light source) may be alternately driven. As such, by alternately driving the first light emission element and the second light emission element, a measurement area of the subject is alternately irradiated with the plurality of lights generated by the first and second light emission elements, and a plurality of signals, generated by the lights being reflected from the subject, may be detected at different times (S201).

Figure 39:
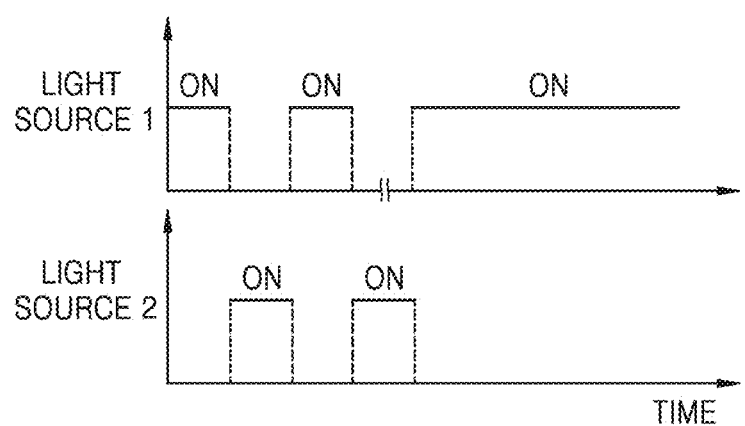
FIG. 39 is a graph explaining a method of detecting biological information, according to another exemplary embodiment.

According to another exemplary embodiment, after the first and second light emission elements are alternately driven at different times for a predetermined time period during an initial stage of measurement, a light emission element having a high SNR is selected based on the detected signals and then the measurement may be performed by driving only the selected light emission element, and FIG. 39 illustrates an example thereof.

Referring to FIG. 39, the first and second light emission elements (first and second light sources) may be alternately driven at different times for only a predetermined time period during an initial stage of measurement, a light emission element having a high SNR is selected based on the detected signals and then the measurement may be performed by driving only the selected light emission element (first light emission element).

Figure 40:
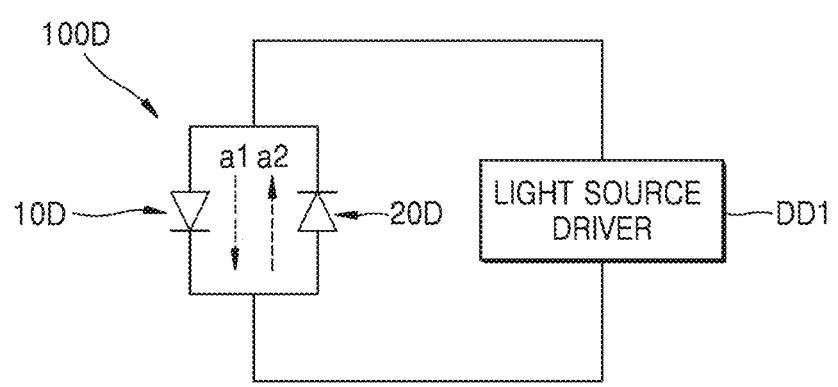
FIG. 40 is a circuit diagram showing an example of a light emission portion for use with the biological signal measurement unit, according to another exemplary embodiment.

To drive the first and second light emission elements alternately, as illustrated in FIGS. 37 to 39, the first and second light emission elements and the light source driver connected thereto may be configured as illustrated in FIG. 40. FIG. 40 is a circuit diagram showing an example of a light emission portion 100D related to the method of detecting biological information of FIGS. 37 to 39.

Referring to FIG. 40, both of a first light emission element 10D and a second light emission element 20D may be diodes. For example, one of the first and second light emission elements 10D and 20D may be an LED and the other thereof may be an LD. In this case, the first light emission element 10D and the second light emission element 20D may be connected in parallel in the opposite direction (opposite rectification direction) to a light source driver DD1. In this case, any one of the first and second light emission elements 10D and 20D may be driven by using the light source driver DD1 in a direction of a current applied to the light emission portion 100D. When the current is applied in a first direction a1, the first light emission element 10D may be driven. When the current is applied in a second direction a2 that is opposite to the first direction a1, the second light emission element 20D may be driven. Accordingly, the first and second light emission elements 10D and 20D may be alternately driven by changing the direction of current applied from the light source driver DD1 to the light emission portion 100D. Accordingly, the circuit structure of FIG. 40 may be applied to implement the methods of FIGS. 37 to 39. However, the circuit structure of FIG. 40 is exemplary and may be changed in various ways. Also, the circuit structure may be modified to use in conjunction with a detection method.

According to another exemplary embodiment, in the operation S100 of FIG. 36, the measurement area of a subject may be simultaneously irradiated with light from at least two light emission elements by simultaneously driving the at least two light emission elements. In this case, in the operation S200 of FIG. 36, the signals may be detected by using a plurality of different light receiving devices. The method may be summarized as shown in a flowchart of FIG. 41.

Figure 41:
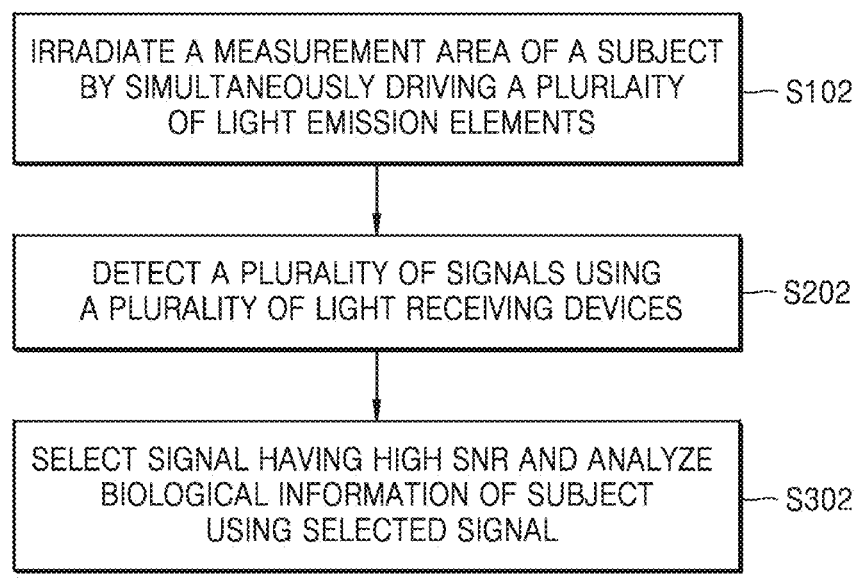
FIG. 41 is a flowchart explaining a method of detecting biological information, according to another exemplary embodiment.

Referring to FIG. 41, a method of detecting biological information according to the present exemplary embodiment may include simultaneously irradiating to a measurement area of a subject with a plurality of lights (incident lights) having different light emission angles by simultaneously driving at least two light emission elements (S102), detecting a plurality of signals generated by light reflected from the measurement area by using a plurality of different light receiving devices (S202), and selecting a signal having a high SNR from among the detected signals and extracting and analyzing biological information of the subject using the selected signal (S302). In the present exemplary embodiment, the light receiving devices in use may include, for example, the first light receiving device PD1 and the second light receiving device PD2 of FIG. 11. Also, the a plurality of light receiving device may correspond to the light receiving device regions 210 and 220 described with reference to FIGS. 17 to 20.

In some cases, instead of selecting a signal having a high SNR in the third operations S300, S301, and S302 of FIGS. 36, 37, and 41, biological information of a subject may be extracted and analyzed by combining the detected signals.

Figure 42:
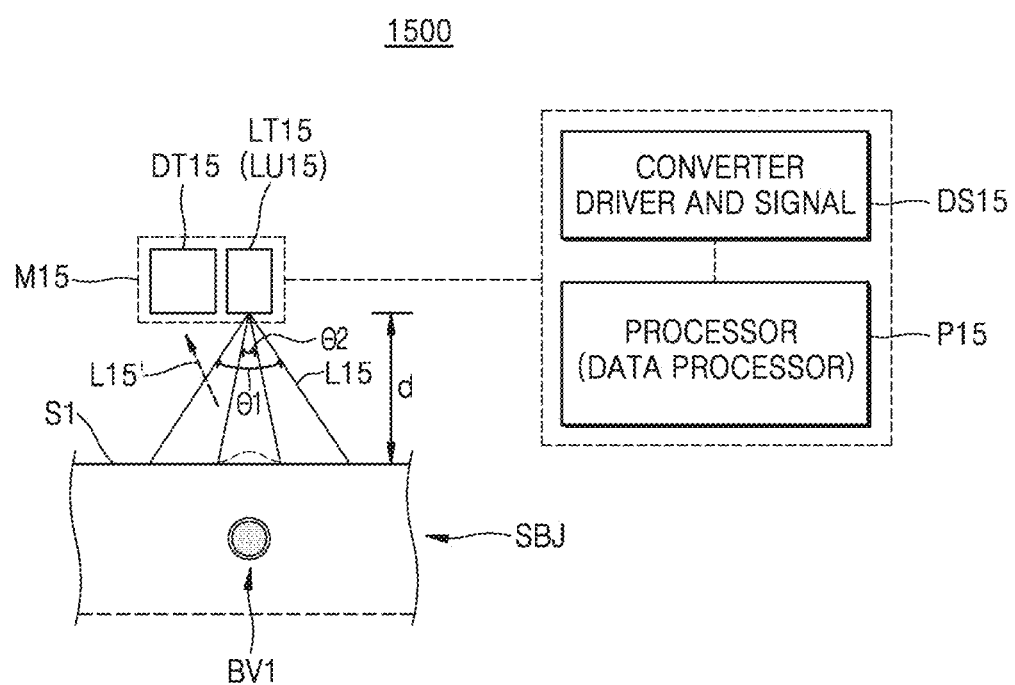
FIG. 42 schematically illustrates a structure of an apparatus for detecting biological information, according to another exemplary embodiment.

FIG. 42 schematically illustrates a structure of a biological information detection apparatus 1500, according to another exemplary embodiment.

Referring to FIG. 42, the biological information detection apparatus 1500 may include a biological signal measurement unit M15 configured to measure a biological signal of the subject SBJ. The biological information detection apparatus 1500 may include a processor (processor unit) P15 comprising a data processor that extracts and analyzes the biological information of the subject SBJ from data measured by the biological signal measurement unit M15. The biological information detection apparatus 1500 may further include a driver and signal converter DS15 that are connected to the biological signal measurement unit M15 and the processor (including the data processor) P15.

A light emission portion LT15 of the biological signal measurement unit M15 may include a light emitting unit LU15 having a variable light emission angle. A light emission angle of the light emitting unit LU15 may vary between a maximum angle θ1 and a minimum angle θ2. The maximum angle θ1 may be determined, for example, to be about 180° or less or about 170° or less. The minimum angle θ2 may be determined, for example, to be about 0° or more or about 5° or more. The ranges of the maximum angle θ1 and the minimum angle θ2 may vary according to the type of a light source used in the light emitting unit LU15. Also, the ranges of the maximum angle θ1 and the minimum angle θ2 may vary according to the structure of the light emission angle control element used in the light emitting unit LU15. A light emission angle of the light emitting unit LU15 may be controlled according to a distance d between the light emission portion LT15 and the subject SBJ. Illumination intensity and the light irradiation area of an incident light L15 radiated by the light emitting unit LU15 to the subject SBJ may be easily controlled by controlling the light emission angle of the light emitting unit LUIS. Accordingly, optimal illumination intensity and an optimal light irradiation area may be easily secured regardless of the distance d.

The biological signal measurement unit M15 may further include a photodetector DT15 that detects light L15' that is irradiated by the light emission portion LT15 onto the subject SBJ and modulated by, for example, reflected or scattered by the subject SBJ. The photodetector DT15 may be arranged adjacent to the light emission portion LT15 and may include at least one light receiving device. For example, a photodiode, a phototransistor, or a charge-coupled device (CCD) may be used as the light receiving device.

Since the structure and function of each of the driver and signal converter DS15 and the processor P15 connected to the biological signal measurement unit M15 may be the same as or similar to those of the driver and signal converter DS10 and the processor P10 described with reference to FIG. 1, detailed descriptions thereof will be omitted.

In the present exemplary embodiment, the same effect as that obtained by the light emission elements LL10 and LL20 of FIG. 1 having the different light emission angles θ1 and θ2 may be obtained by using the light emitting unit LU15 having a variable light emission angle.

The light emitting unit LU15 of FIG. 42 may include a predetermined light source and a light emission angle control element configured to control the light emission angle of the predetermined light source. A structure of the light emitting unit LU15 is described below with reference to FIG. 43.

Figure 43:
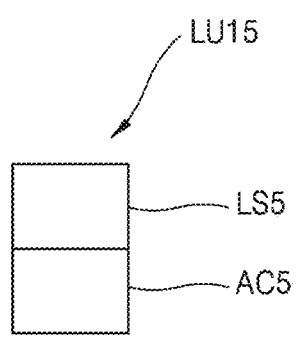
FIG. 43 illustrates a structure of the light emitting unit of FIG. 42, according to an exemplary embodiment.

FIG. 43 illustrates a structure of the light emitting unit LU15 of FIG. 42, according to an exemplary embodiment. Referring to FIG. 43, the light emitting unit LU15 may include a light source LS5 and a light emission angle control element AC5 to control a light emission angle of the light source LS5. The light source LS5 may be, for example, an LED or an LD, or other light emitting source (light emitting device). The light emission angle control element AC5 may include, for example, a variable focusing lens. In this case, the light emission angle control element AC5 may include an auto focusing module (AFM) using a voice coil motor (VCM), a liquid lens using electrowetting, or a variable focal length microlens comprising liquid crystal.

Figure 44:
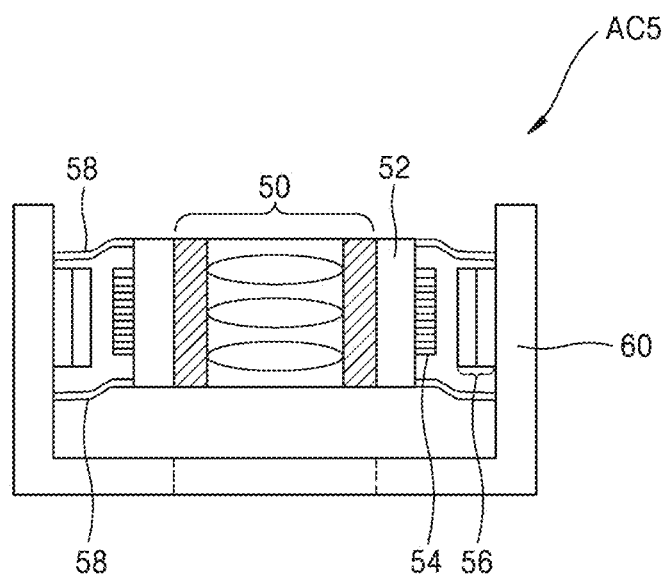
FIG. 44 is a cross-sectional view showing an example of a structure of a light emission angle control element of FIG. 43.

FIG. 44 is a cross-sectional view showing an example of a structure of the light emission angle control element AC5 of FIG. 43. In the present exemplary embodiment, the light emission angle control element AC5 has an AFM structure.

Referring to FIG. 44, the light emission angle control element AC5 may include a housing structure 60 having an AFM structure, and a lens module 50 may be provided in the housing structure 60. The lens module 50 may include at least one lens and a lens barrel. The lens module 50 may be provided in a lens holder 52. The lens holder 52 may be a type of bobbin. A coil 54 may surround the lens holder 52, and a magnetic member 56 may be provided corresponding to the coil 54. A spring member 58 may be provided between the lens holder 52 and the housing structure 60. The spring member 58 may be provided at upper and lower portions of the lens holder 52. The spring member 58 may be, for example, a plate spring. The lens module 50 may be moved up and down according to the direction of current applied to the coil 54.

The light emission angle control element AC5 of FIG. 44 may be located under the light source LS5 of FIG. 43, and may be in an orientation which is upside-down as compared to the orientation as illustrated in FIG. 44. The AFM structure of FIG. 44 is exemplary and may be modified in various ways. Also, instead of the AFM structure, the light emission angle control element AC5 may include a liquid lens using electrowetting or a variable focal length microlens using liquid crystal. Since the structures of a liquid lens and a variable focal length microlens are known, detailed descriptions thereof are omitted.

According to the present exemplary embodiment, a light emission portion may include two or more light emitting units (light sources), and a photodetector may include two or more light receiving devices. In the following description, various plane structures (array structures) of the biological signal measurement unit are described below with reference to FIGS. 45 to 48.

Figure 45:
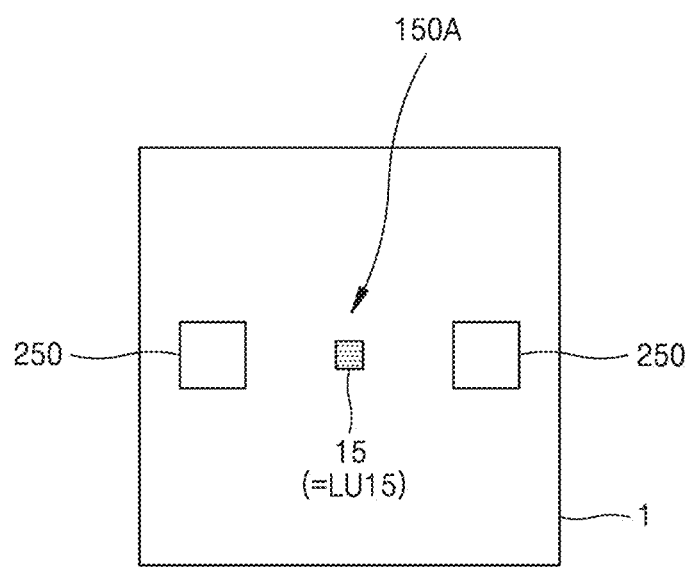
FIG. 45 is a plan view showing a structure of a biological signal measurement unit for use with the apparatus for detecting biological information, according to another exemplary embodiment.

FIG. 45 is a plan view showing a structure of a biological signal measurement unit for use with the biological information detection apparatus, according to another exemplary embodiment.

Referring to FIG. 45, a light emission portion 150A may include a light emitting unit 15 having variable light emission angles. The light emitting unit 15 may correspond to the light emitting unit LU15 of FIG. 42. A plurality of light receiving devices 250 may be provided around the light emission portion 150A. For example, two light receiving devices 250 may be provided at opposite sides of the light emission portion 150A. A plurality of light receiving devices 250 may form a single photodetector. The light emission portion 150A and the light receiving devices 250 are provided on a substrate 1. The substrate 1 may be, for example, a PCB, or another type of substrate. The substrate 1 may be a support.

Figure 46:
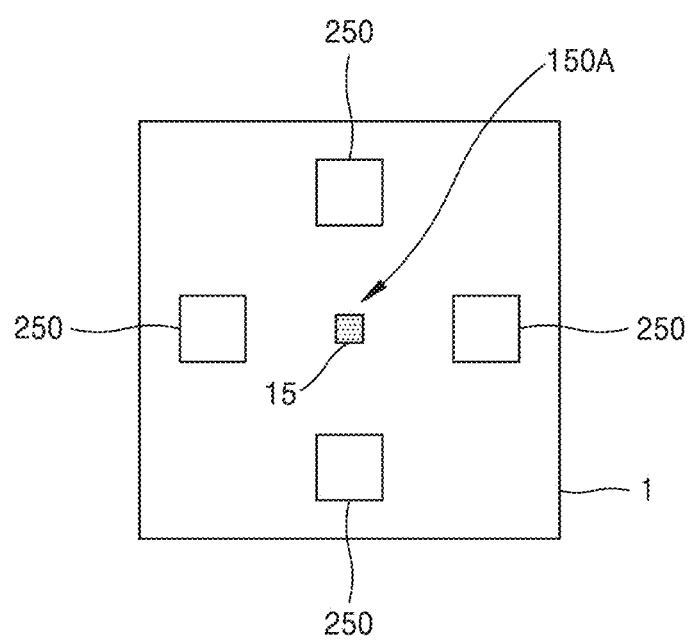
FIG. 46 is a plan view showing a structure of a biological signal measurement unit for use with the apparatus for detecting biological information, according to another exemplary embodiment.

Although FIG. 45 illustrates a case in which the two light receiving devices 250 are provided at opposite sides of the light emission portion 150A, as illustrated in FIG. 46, four light receiving devices 250 may be provided at upper, lower, left, and right sides, respectively, of the light emission portion 150A. In other words, one of the light receiving devices 250 may be provided at each of at least four positions around the light emission portion 150A.

Figure 47:
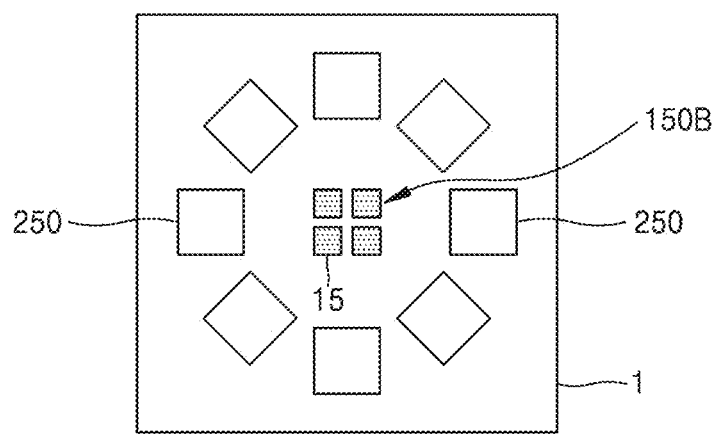
FIG. 47 is a plan view showing a structure of a biological signal measurement unit for use with the apparatus for detecting biological information, according to another exemplary embodiment.

In FIGS. 45 and 46, the light emission portion 150A may include a plurality of light emitting units 15. Also, the number and arrangement method of the light receiving devices 250 may vary. Referring to FIG. 47, a light emission portion 150B may have a structure in which a plurality of light emitting units 15 are arranged in a 2D array. Also, the light receiving devices 250 may be arranged forming an annular shape around the light emission portion 150B.

Figure 48:
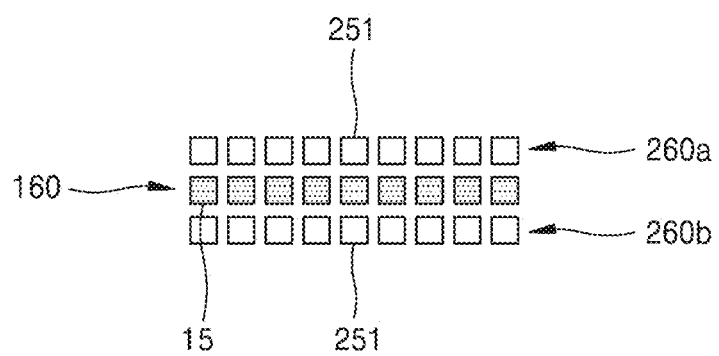
FIG. 48 is a plan view showing a structure of a biological signal measurement unit for use with the apparatus for detecting biological information, according to another exemplary embodiment.

FIG. 48 is a plan view showing a structure of a biological signal measurement unit, according to another exemplary embodiment.

Referring to FIG. 48, a light emission portion 160 may have a structure in which a plurality of light emitting units 15 form at least one line. A plurality of light receiving devices 251 may be provided around the light emission portion 160. The light receiving devices 251 may be arranged forming an array at at least one side of the light emission portion 160. For example, light receiving device arrays 260a and 260b, each including a plurality of light receiving devices 251, may be provided, respectively, at opposite sides of the light emission portion 160, as shown in FIG. 48. Although FIG. 48 illustrates that the light emitting units 15 of the light emission portion 160 form one line, an array structure having two or more lines may be used.

The plane structures (array structures) described with reference to FIGS. 45 to 48 are exemplary and the structures may be modified in various ways to the structures described with reference to FIGS. 12 to 23, or structures similar thereto.

Figure 49:
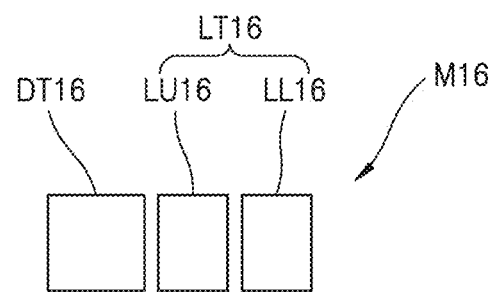
FIG. 49 illustrates a biological signal measurement unit for use with the apparatus for detecting biological information, according to another exemplary embodiment.
Figure 50:
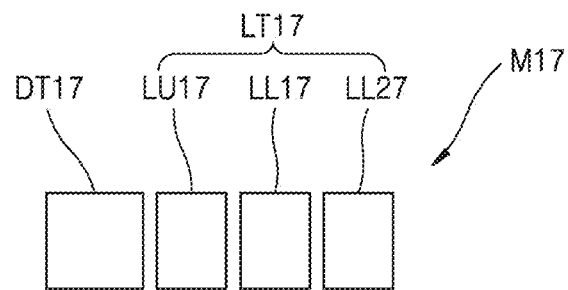
FIG. 50 illustrates a biological signal measurement unit for use with the apparatus for detecting biological information, according to another exemplary embodiment.

According to another exemplary embodiment, the biological signal measurement unit M15 of FIG. 42 may further include at least one light emission element having a light emission angle, which is fixed on the light emission portion LT15, and FIGS. 49 and 50 illustrate example thereof.

Referring to FIG. 49, in a biological signal measurement unit M16, a light emission portion LT16 may include a light emitting unit LU16 having variable light emission angles and a light emission element LL16 having a fixed light emission angle. The light emission element LL16 may correspond to the first light emission element LL10 or the second light emission element LL20 of FIG. 1, or may be similar thereto. The light emitting unit LU16 may correspond to the light emitting unit LU15 of FIG. 42, or may be similar thereto. The biological signal measurement unit M16 may include a photodetector DT16.

Referring to FIG. 50, in a biological signal measurement unit M17, a light emission portion LT17 may include a light emitting unit LU17 having variable light emission angles and a plurality of light emission elements LL17 and LL27 having a fixed light emission angle. The light emission elements LL17 and LL27 may include the first light emission element LL17 and the second light emission element LL27. The first light emission element LL17 and the second light emission element LL27 may correspond to the first light emission element LL10 and the second light emission element LL20 of FIG. 1, respectively, or may be similar thereto. The light emitting unit LU17 may correspond to the light emitting unit LU15 of FIG. 42, or may be similar thereto. The biological signal measurement unit M17 may include a photodetector DT17.

As illustrated in FIGS. 49 and 50, when the light emitting unit LU16 or LU17 having variable light emission angle and at least one of light emission elements LL16, LL17, and LL27 having a fixed light emission angle are used together, the measurement may be performed while changing the light emission angle of the light emitting units LU16 or LU17, and also the measurement may be performed using the light emission elements LL16, LL17, and LL27, which may be advantageous to the measurement of a biological signal in many aspects.

Figure 51:
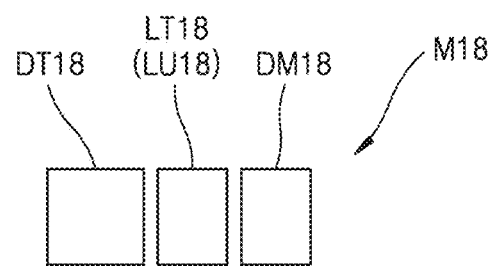
FIG. 51 illustrates a biological signal measurement unit for use with the apparatus for detecting biological information, according to another exemplary embodiment.

According to another exemplary embodiment, the biological signal measurement unit M15 of FIG. 42 may further include a distance measuring sensor that is adjacent to the light emission portion LT15, and FIG. 51 illustrates an example thereof.

Referring to FIG. 51, a biological signal measurement unit M18 may include a light emission portion LU18 and a photodetector DT18, and may further include a distance measuring sensor DM18 that is adjacent to the light emission portion LU18. The light emission portion LU18 and the photodetector DT18 may correspond to the light emission portion LU15 and the photodetector DT15 of FIG. 42, respectively. The light emission portion LU18 may be a light emitting unit having a variable light emission angle. The distance measuring sensor DM18 may be a device to measure a distance d of FIG. 42 between the light emission portion LU18 and a subject (not shown) to be measured. The distance measuring sensor DM18 may have a structure that is the same as or similar to a proximity sensor. A distance between the light emitting unit LU18, or a light source included therein, and the subject may be measured using the distance measuring sensor DM18, and a light emission angle of the light emitting unit LU18 may be controlled according to the measured distance. The use of the distance measuring sensor DM18 is optional. The distance measuring sensor DM18 of FIG. 51 may be used with the biological signal measurement units M16 and M17 of FIGS. 49 and 50.

Figure 52:
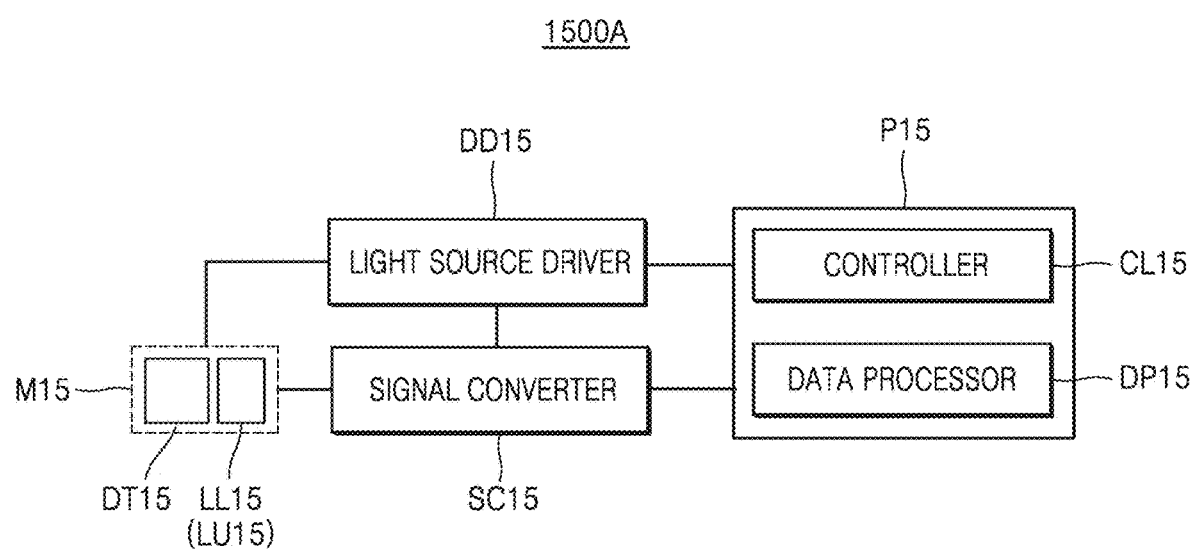
FIG. 52 is a block diagram showing a structure of the apparatus for detecting biological information FIG. 42, according to an exemplary embodiment.

FIG. 52 is a block diagram showing a structure of the biological information detection apparatus 1500 of FIG. 42.

Referring to FIG. 52, a biological information detection apparatus 1500A may include the biological signal measurement unit M15. The biological signal measurement unit M15 may have the structure of the biological signal measurement unit M15 described with reference to FIG. 42 or any one of various structures modified therefrom. The biological information detection apparatus 1500A may include a processor (processor unit) P15 having a data processor DP15 that extracts and analyzes biological information of the subject SBJ from data measured by the biological signal measurement unit M15. The processor P15 may further include a controller CL15 to control an overall operation of the biological information detection apparatus 1500A. The biological information detection apparatus 1500A may further include a light source driver DD15 connected to the biological signal measurement unit M15. The light source driver DD15 may be connected to the processor P15. The biological information detection apparatus 1500A may further include a signal converter SC15 that is connected between the biological signal measurement unit M15 and the processor P15. The signal converter SC15 may be connected to the light source driver DD15. Although not illustrated, the processor P15 may further include a data communication unit and/or memory. The light source driver DD15, the signal converter SC15, the controller CL15, and the data processor DP15 of FIG. 52 may be similar to the light source driver DD10, the signal converter SC10, the controller CL10, and the data processor DP10 of FIG. 29. Also, in the present exemplary embodiment, a light emission angle of the light emitting unit LU15 may be automatically controlled as necessary using the controller CL15 and the light source driver DD15.

Figure 53:
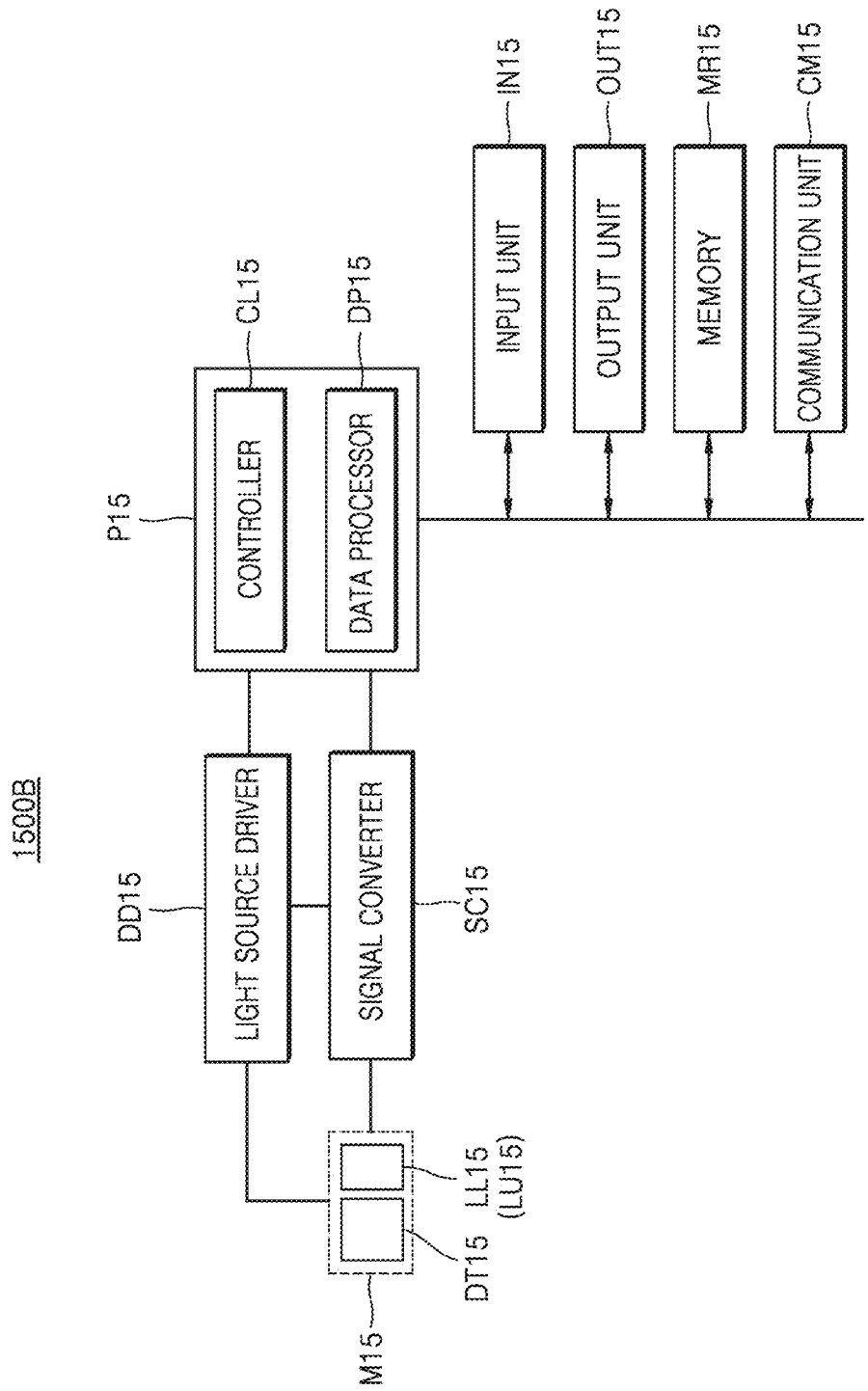
FIG. 53 is a block diagram showing a structure of the apparatus for detecting biological information FIG. 42, according to another exemplary embodiment.

FIG. 53 is a block diagram showing a structure of a biological information detection apparatus 1500B, according to another exemplary embodiment.

Referring to FIG. 53, as described in FIG. 52, the biological information detection apparatus 1500B may include the biological signal measurement unit M15, the light source driver DD15, the signal converter SC15, and the processor P15. The biological information detection apparatus 1500B according to the present exemplary embodiment may further include an input unit IN15, an output unit OUT15, a memory MR15, and a communication unit CM15, which are connected to the processor P15. The input unit IN15, the output unit OUT15, the memory MR15, and the communication unit CM15 may be the same as or similar to the input unit IN10, the output unit OUT10, the memory MR10, and the communication unit CM10 described in FIG. 30, respectively. Also, the structure of FIG. 53 may be changed in various ways as described with reference to FIGS. 31 to 33.

In the following description, the biological information detection methods according to the present exemplary embodiments are described below.

Figure 54:
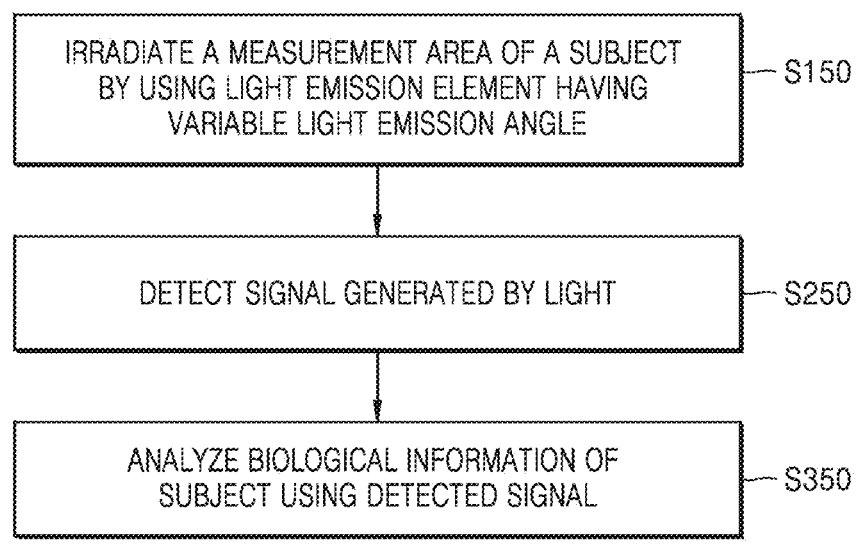
FIG. 54 is a flowchart explaining a method of detecting biological information, according to another exemplary embodiment.

FIG. 54 is a flowchart explaining a method of detecting biological information, according to another exemplary embodiment. The following description with reference to FIG. 54 is related to the biological information detection apparatus described with reference to FIGS. 42 to 53 and relevant descriptions thereof. Accordingly, the method of FIG. 54 may be understood based on the descriptions of FIGS. 42 to 53.

Referring to FIG. 54, a method of detecting biological information according to the present exemplary embodiment may include irradiating a measurement area of a subject with light from at least one light emission element having a variable light emission angle (viewing angle) (S150), detecting a signal generated from light reflected from the measurement area (S250), and extracting and analyzing biological information of the subject using the detected signal (S350). In the operation S150, the at least one light emission element having a variable light emission angle (viewing angle) may correspond to, for example, the light emitting unit LU15 of FIG. 42. The signal detection of the operation S250 may be performed by, for example, the photodetector DT15 of FIG. 42. The biological information extraction and analysis of the operation S350 may be performed by, for example, the data processor DP15 of FIGS. 42 and 52.

According to the present exemplary embodiment, in the operation S150, a distance between the light emitting unit (light source) and the subject may be measured and a light emission angle of the light emitting unit may be changed according to a measured distance. The method may be summarized as shown in a flowchart of FIG. 55.

Figure 55:
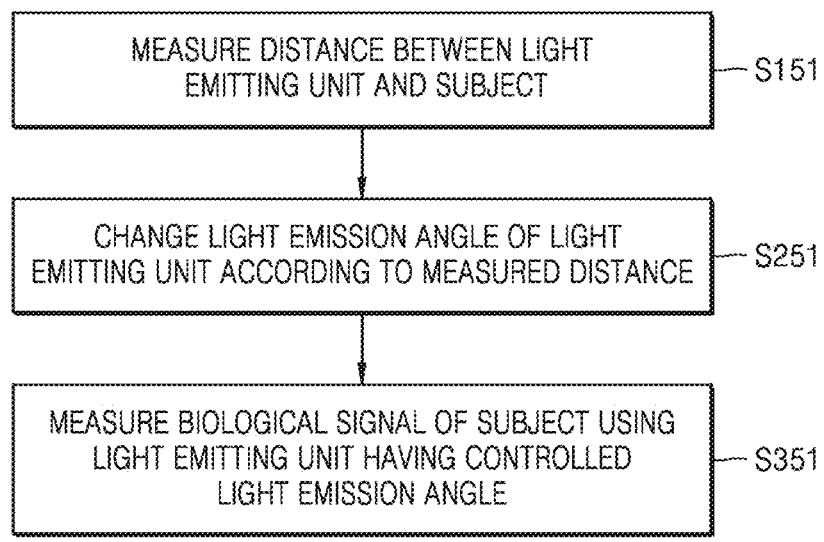
FIG. 55 is a flowchart explaining a method of detecting biological information, according to another exemplary embodiment.

Referring to FIG. 55, a method of detecting biological information according to the present exemplary embodiment may include measuring a distance between the light emitting unit (light source) and the subject (S151), changing a light emission angle of the light emitting unit according to the measured distance (S251), and measuring a biological signal of the subject using the light emitting unit having the changed (controlled) light emission angle (S351).

In the operation S151, there may be various methods to measure the distance between the light emitting unit (light source) and the subject. For example, when a distance between the light emitting unit (light source) and a skin surface of the subject is relatively long, a direct current (DC) level of a detected signal, for example, a pulse wave signal, decreases. When the distance is relatively short, the DC level of a detected signal increases. As the DC level, that is, the height of a DC component, is analyzed using the above principle, the distance between the light emitting unit (light source) and the subject may be calculated. The relation between the above-described distance between the light emitting unit (light source) and the subject and the DC level of a detected signal may be represented by a graph of FIG. 56.

Figure 56:
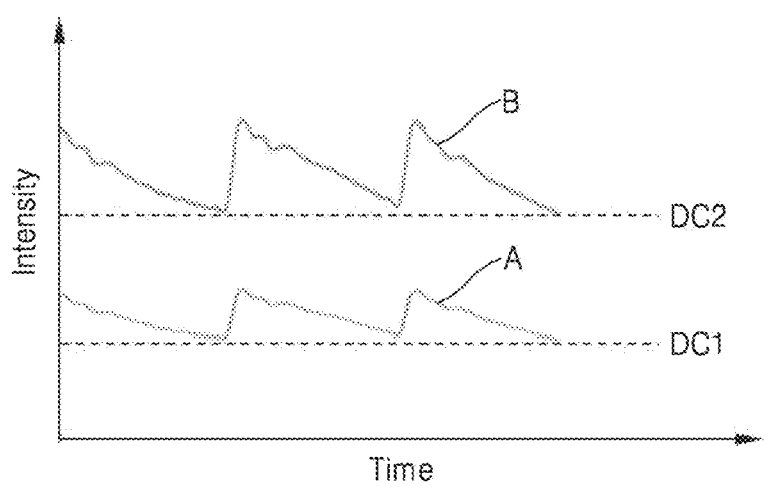
FIG. 56 is a graph showing two signals detected according to an exemplary embodiment and direct current (DC) levels thereof.

Referring to FIG. 56, a graph A denotes a detected signal corresponding to a case in which the distance between the light emitting unit (light source) and the subject is relatively long, and a graph B denotes a detected signal corresponding to a case in which the distance between the light emitting unit (light source) and the subject is relatively short. When the distance between the light emitting unit (light source) and the subject is relatively long (graph A), a detected signal may have a relatively low DC level DC1, and when the distance is relatively short (graph B), a detected signal may have a relatively high DC level DC2. Accordingly, the distance between the light emitting unit (light source) and the subject may be calculated by measuring and analyzing the DC level of a detected signal. Accordingly, the data processor of the processor P15 of FIG. 42 may further include a DC component analysis unit. Similarly, the data processor of the processor P10 of FIG. 1 may further include a DC component analysis unit. However, the method of measuring a distance between the light emitting unit (light source) and the subject may be changed in various ways. As an example, as illustrated in FIG. 51, when the distance measuring sensor DM18 is in use, the distance may be directly measured using the distance measuring sensor DM18.

As such, after the distance between the light emitting unit (light source) and the subject is measured, a light emission angle of the light emitting unit (light source) is adjusted to an appropriate value according to the measurement, and then, a biological signal is measured using the adjusted light emission angle. Accordingly, optimal illumination intensity and an optimal light irradiation area may be easily obtained, and as a result, accuracy and reliability in the measurement may be greatly improved.

Figure 57:
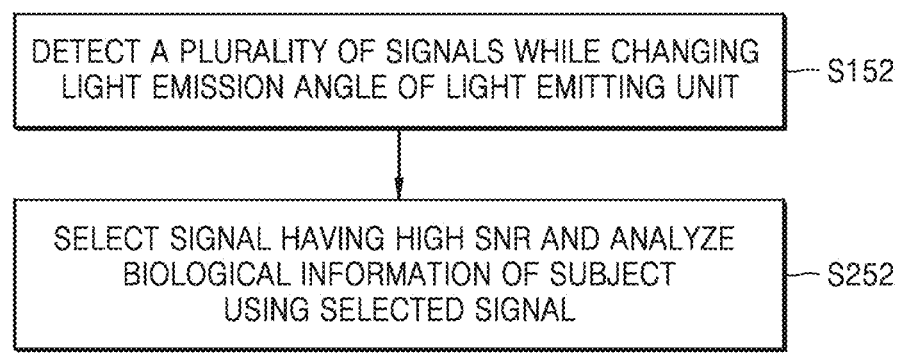
FIG. 57 is a flowchart explaining a method of detecting biological information, according to another exemplary embodiment.

According to another exemplary embodiment, as illustrated in FIG. 57, after a plurality of signals corresponding to a plurality of light emission angles are detected while a light emission angle of a light emitting unit having a variable light emission angle is changed (S152), and a signal having a high SNR is selected from among the detected signals and biological information of the subject may be extracted and analyzed by using the selected signal (S252). In the method, the distance measurement operation may be omitted and, after a plurality of signals are detected while freely arbitrarily changing a light emission angle of the light emitting unit, a signal having a high SNR is selected from among the signals and used for extracting and analyzing biological information. In some cases, in the operation S252, instead of selecting a signal having a high SNR, the biological information of a subject may be extracted and analyzed by combining detected signals.

In addition, in the biological information detection apparatus 1000 of FIG. 1, a variety of factors (variables) may be taken into consideration in determining a range of the first light emission angle θ1 and a range of the second light emission angle θ2. For example, considering the distance between the first light emission element LL10 and the photodetector DT10, the distance between the first light emission element LL10 and the subject SBJ, a divergence angle of diffuse reflection of the first incident light L10 on the surface (body surface) S1, and a width of an effective signal generation area of the surface S1, a range of the first light emission angle θ1 may be determined. Similarly, considering the distance between the second light emission element LL20 and the photodetector DT10, the distance between the second light emission element LL20 and the subject SBJ, a divergence angle of diffuse reflection of the second incident light L20 on the surface S1, and a width of an effective signal generation area of the surface S1, the range of the second light emission angle θ2 may be determined. Also, in the biological information detection apparatus 1500 of FIG. 42, when a light emission angle range of the light emitting unit LU15 is determined, a variety of factors (variables) such as the distance between the light emitting unit LU15 and the photodetector DT15, the distance between the light emitting unit LU15 and the subject SBJ, a divergence angle of diffuse reflection of the incident light L15 on the surface S1, and a width of an effective signal generation area of the surface S1 may be taken into consideration the surface S1.

Figure 58:
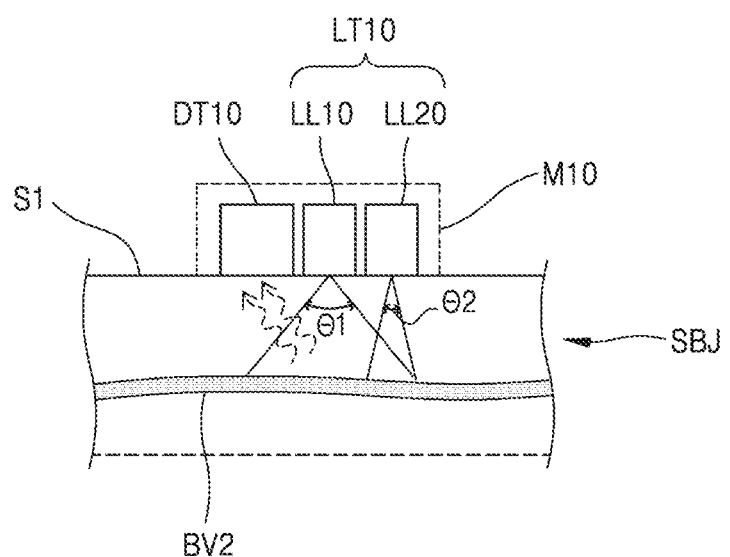
FIG. 58 illustrates an apparatus for and method of detecting biological information, according to another exemplary embodiment.
Figure 59:
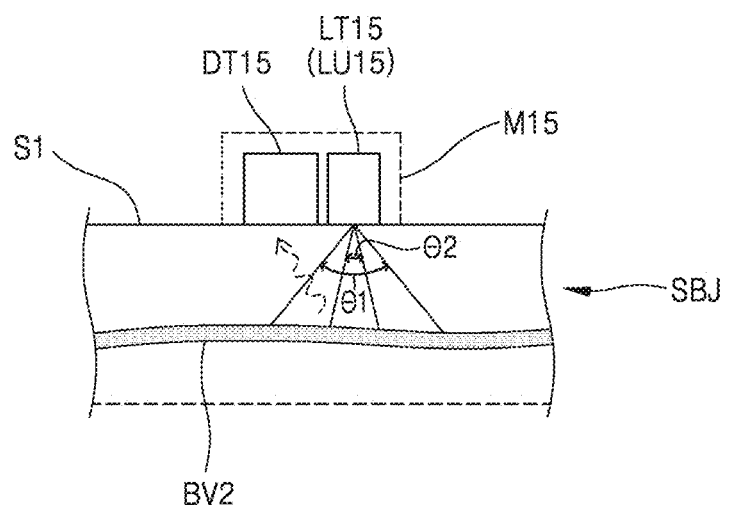
FIG. 59 illustrates an apparatus and method of detecting biological information, according to another exemplary embodiment.

According to another exemplary embodiment, the measurement may be performed in a state in which the biological signal measurement unit approaches or is in contact with an effective measurement area of the subject, and FIGS. 58 and 59 illustrate examples thereof.

FIG. 58 illustrates a case in which the measurement is performed while the biological signal measurement unit M10 is in contact with an effective measurement surface of the surface S1 of the subject SBJ, as described with reference to FIG. 1. FIG. 59 illustrates a case in which the measurement is performed while the biological signal measurement unit M15 is in contact with an effective measurement surface of the surface S1 of the subject SBJ, as described with reference to FIG. 42.

The exemplary embodiments illustrated in FIGS. 58 and 59 may correspond to a case of detecting a photoplethysmogram (PPG) signal of the subject SBJ. The PPG signal may be measured by using the principle that an optical signal that is reflected or scattered varies according to a change in the volume of blood existing in a blood vessel BV2 of the subject SBJ. Since reflection and scattering of light decreases when an amount of blood is relatively large and increases when an amount of blood is relatively small, the PPG signal may be changed according to contraction and relaxation of the blood vessel BV2.

When the light emission elements LL10 and LL20 having different light emission angles are used as in FIG. 58, or the light emitting unit LU15 having a variable light emission angle is used as in FIG. 59, accuracy in the measurement of a PPG signal may be improved. For example, when skin tissues of the subject SBJ in FIG. 58 are relatively thin, the first light emission element LL10 having a relatively large light emission angle is mainly used for the measurement. When the skin tissues of the subject SBJ in FIG. 58 are relatively thick, the second light emission element LL20 having a relatively small light emission angle is mainly used for the measurement. When the skin tissues of the subject SBJ are relatively thick, intensity of light arriving at the blood vessel BV2 may be decreased. Accordingly, the use of the second light emission element LL20 having a relatively small light emission angle may be advantageous for the measurement. Similarly, in the exemplary embodiment of FIG. 59, when the light emission angle of the light emitting unit LU15 is adjusted according to the thickness of the skin tissues of the subject SBJ, accuracy in the measurement may be improved. Also, after a plurality of signals are detected using the light emission elements LL10 and LL20 of FIG. 58, or while changing a light emission angle of the light emitting unit LU15 of FIG. 59, signals having a high SNR are selected from among the detected signals and then biological information may be analyzed, or biological information may be analyzed by combining data from the signals.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments. For example, one of ordinary skill in the art to which the present inventive concept pertains would understand that the apparatuses and systems for detecting biological information and the methods of detecting biological information described with reference to FIGS. 1 to 59 may be changed in various ways. For example, the light emission direction of the first light emission element LL10 and the light emission direction of the second light emission element LL20 may form a predetermined angle instead of being parallel to each other. The photodetector DT10 may be located at a height different from those of light emission elements LL10 and LL20. The positional relationship between the photodetector DT10 and the light emission portion LT10 may be changed in various ways. Also, a measurement unit that detects light passing through (i.e., transmitted) a predetermined portion of a subject may be used, or a measurement unit that detects a biological signal other than a surface pulse wave signal or a PPG signal of a subject may be used. While one or more exemplary embodiments have been described with reference to the figures, it will be understood by those of ordinary skill in the art that various changes in form and details may be made therein without departing from the spirit and scope as defined by the following claims.

What is claimed is:

1. An apparatus for detecting biological information, the apparatus comprising:
    a biological signal measurement unit comprising a light emission portion and a photodetector, the light emission portion comprising at least one light emitting unit, the at least one light emitting unit comprising a light source and a light emission angle control element configured to change a light emission angle of the light source,
        wherein the photodetector is configured to detect light generated by the light emission portion and modulated by a subject, and
        wherein the biological signal measurement unit is further configured to generate a plurality of signals of the subject by using the light detected by the photodetector while the light emission angle control element arbitrarily changes the light emission angle of the light source of the at least one light emitting unit; and
    a data processor configured to extract and analyze the biological information of the subject from data corresponding to a signal selected from among the plurality of signals generated by the biological signal measurement unit.

2. The apparatus of claim 1, wherein the light emission angle control element comprises a variable focus lens.

3. The apparatus of claim 2, wherein the light emission angle control element comprises one of an auto focusing module (AFM) comprising a voice coil motor (VCM), a liquid lens comprising an electrowetting unit, and a variable focal length microlens comprising liquid crystal.

4. The apparatus of claim 1, wherein the data processor is further configured to select, from the plurality of signals, a signal having a signal-to-noise ratio (SNR) higher than that of at least one another signal of the plurality of signals, and extract and analyze the biological information of the subject from data corresponding to the selected signal.

5. The apparatus of claim 1, wherein the photodetector comprises a plurality of light receiving devices, and
    the plurality of light receiving devices are disposed in an array around at least a part of the light emission portion.

6. The apparatus of claim 1, wherein the at least one light emitting unit comprises a plurality of light emitting units.

7. The apparatus of claim 1, wherein the light emission portion further comprises at least one another light emission element having a fixed light emission angle.

8. The apparatus of claim 1, wherein the biological signal measurement unit is configured to measure at least one of a surface pulse wave and a photoplethysmogram (PPG) of the subject.

9. The apparatus of claim 1, wherein the biological information analyzed by the data processor comprises at least one of a blood pressure, a heart rate, a blood oxygen saturation, a blood vessel elasticity, a blood flow rate, and arterial stiffness.

10. A method of detecting biological information, the method comprising:
    outputting light from at least one light emitting unit, thereby irradiating a measurement area of a subject, wherein the at least one light emitting unit comprises a light source and a light emission angle control element configured to change a light emission angle of the light source;
    detecting light output by the at least one light emitting unit and modulated by the subject;
    generating a plurality of signals from the detected light, which is output by the at least one light emitting unit while the light emission angle of the light source of the at least one light emitting unit is arbitrarily changed; and
    extracting and analyzing the biological information of the subject using a signal selected from among the generated plurality of signals.

11. The method of claim 10, further comprising:
    selecting, from the plurality of signals, a signal having a signal-to-noise ratio (SNR) higher than that of at least one another signal of the plurality of signals,
    wherein the extracting and analyzing comprises extracting and analyzing the biological information of the subject using the selected signal.

12. The method of claim 10, wherein the light emission angle control element comprises a variable focusing lens.

* * * * *